United States Patent
Vidal Juan et al.

(10) Patent No.: US 7,060,824 B2
(45) Date of Patent: Jun. 13, 2006

(54) PYRROLOTRIAZOLOPYRIMIDINONE DERIVATIVES

(75) Inventors: Bernat Vidal Juan, Barcelona (ES); Cristina Esteve Trias, Barcelona (ES); Jordi Gracia Ferrer, Barcelona (ES); José Manuel Prieto Soto, Barcelona (ES)

(73) Assignee: Almirall Prodesfarma, S.A., Barcelona (ES)

( * ) Notice: Subject to any disclaimer, the term of this patent is extended or adjusted under 35 U.S.C. 154(b) by 191 days.

(21) Appl. No.: 10/343,934

(22) PCT Filed: Aug. 1, 2001

(86) PCT No.: PCT/EP01/08904

§ 371 (c)(1),
(2), (4) Date: Aug. 15, 2003

(87) PCT Pub. No.: WO02/12246

PCT Pub. Date: Feb. 14, 2002

(65) Prior Publication Data

US 2004/0019034 A1    Jan. 29, 2004

(30) Foreign Application Priority Data

Aug. 9, 2000  (ES) ................. 200002039

(51) Int. Cl.
*C07D 487/14*   (2006.01)
*A61K 31/519*   (2006.01)
(52) U.S. Cl. ................. 544/251; 544/280; 514/267
(58) Field of Classification Search ............... 514/267; 544/251, 280
See application file for complete search history.

(56) References Cited

FOREIGN PATENT DOCUMENTS

WO    WO 99/62905    12/1999

*Primary Examiner*—Thomas C. McKenzie

(74) *Attorney, Agent, or Firm*—Venable LLP; Marina V. Schneller

(57) ABSTRACT

This invention relates to new therapeutically useful 8-(disubstituted)phenyl-6,9-dihydro-5H-pyrrolo[2,3-e][1,2,4]triazolo[4,3-c]pyrimidine-5-one and 8-phenyl-6,9-dihydro-5H-pyrrolo[3,2-e][1,2,4]triazolo[4,3-c]pyrimidine-5-one derivatives of formula (I): wherein: —X—C—Y— represents (a) or (b) to processes and intermediates for their preparation, to pharmaceutical compositions containing them and to their medical uses as potent and selective inhibitors of phosphodiesterase 5 (PDE 5).

15 Claims, No Drawings

PYRROLOTRIAZOLOPYRIMIDINONE DERIVATIVES

This application relies on the benefit of Spanish application number 200002039, filede Aug. 9, 2000, and on the International application PCT/EP01/8904, filed Aug. 1, 2001, each of which is incorporated by reference herein.

This invention relates to new therapeutically useful pyrrolotriazolopyrimidinone derivatives, to processes for their preparation and to pharmaceutical compositions containing them.

We have now found that certain 8-(disubstituted)phenyl-6,9-dihydro-5H-pyrrolo[2,3-e][1,2,4]triazolo[4,3-c]pyrimidine-5-one and 8-phenyl-6,9-dihydro-5H-pyrrolo[3,2-e][1,2,4]triazolo[4,3-c]pyrimidine-5-one derivatives are potent and selective inhibitors of phosphodiesterase 5 (PDE 5), and have efficacy in the treatment of angina, hypertension, congestive heart failure, stroke, asthma, male erectile dysfunction, female sexual dysfunction, premature labour, dysmenorrhea, BPH, incontinence, glaucoma and irritable bowel syndrome.

Accordingly, the present invention provides compounds which are 8-phenylpyrrolotriazolopyrimidine derivatives of formula (I):

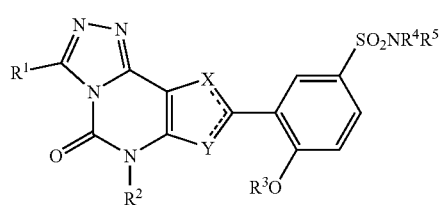

wherein: —X—C—Y— represents

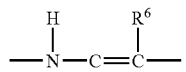

as in formula (II)

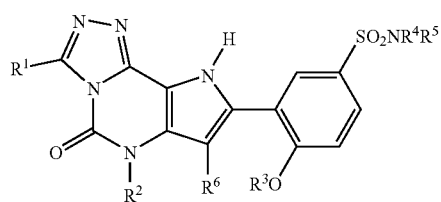

or —X—C—Y— represents

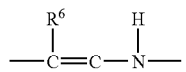

as in formula (III)

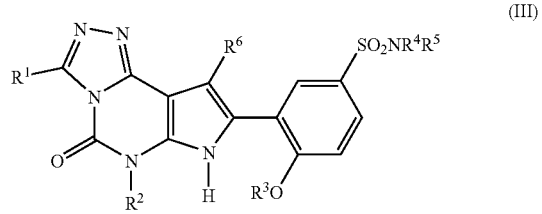

$R^1$, $R^2$ and $R^3$ each independently represent: hydrogen; an alkyl group which is unsubstituted or substituted by hydroxy, alkoxy, alkylthio, amino, mono- or di-alkylamino, hydroxycarbonyl, alkoxycarbonyl, acylamino, carbamoyl or alkylcarbamoyl groups; or a group of formula

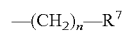

wherein n is an integer from 0 to 4 and $R^7$ represents: a cycloalkyl group which may be unsubstituted or substituted by one or more halogen atoms or alkyl, hydroxy, alkylenedioxy, alkoxy, amino, mono- or di-alkylamino, alkylamido, nitro, cyano or trifluoromethyl groups; a phenyl group which may be unsubstituted or substituted by one or more halogen atoms or alkyl, hydroxy, alkylenedioxy, alkoxy, amino, mono- or di-alkylamino, nitro, cyano or trifluoromethyl groups; or a 3 to 7-membered ring comprising from 1 to 4 heteroatoms selected from nitrogen, oxygen and sulphur, which ring may be unsubstituted or substituted by one or more halogen atoms or hydroxy, alkoxy, phenyl, alkoxycarbonyl, amino, mono-alkylamino, di-alkylamino or hydroxycarbonyl groups or one or more alkyl groups which may be unsubstituted or substituted by one or more halogen atoms or hydroxy, alkoxy, hydroxyalkoxy, phenyl, alkoxycarbonyl, amino, mono- or di-alkylamino or hydroxycarbonyl groups;

either $R^4$ and $R^5$ together with the nitrogen atom to which they are attached form a 3 to 7-membered ring comprising a total of from 1 to 4 heteroatoms selected from nitrogen, oxygen and sulphur, which ring may be unsubstituted or substituted by one or more halogen atoms or hydroxy, oxoalkyl, carbamoyl, hydroxycarbonyl, alkoxycarbonyl, trifluoroacetyl, amino, mono- or di-alkylamino groups and/or an alkylene group and/or one or more alkyl groups, wherein said alkylene group and said alkyl groups may in turn be unsubstituted or substituted by one or more hydroxy, alkoxy, hydroxyalkoxy, amino or mono- or di-alkylamino groups, or $R^4$ and $R^5$ independently represent hydrogen, an amidino group or an alkyl, alkenyl or alkynyl group which may be unsubstituted or substituted by one or more halogen atoms or hydroxy, alkoxy, alkylthio, amino, mono- or di-alkylamino groups, or $R^4$ represents hydrogen or an alkyl group and $R^5$ represents a group of formula —$(CH_2)_n$—$R^7$ wherein n and $R^7$ are defined above, $R^6$ represents a hydrogen or halogen atom, or a nitro or alkoxycarbonyl group, or an alkyl group which is unsubstituted or substituted by one or more hydroxy, alkoxy, alkylthio, amino, mono- or di-alkylamino, hydroxycarbonyl, alkoxycarbonyl, acylamino, carbamoyl or alkylcarbamoyl groups, or a pharmaceutically acceptable salt thereof.

When $R^4$ and $R^5$, together with the nitrogen atom to which they are attached, form a 3 to 7-membered ring, said ring may be unsubstituted or substituted by one or more halogen atoms or hydroxy, oxoalkyl, carbamoyl, hydroxycarbonyl, alkoxycarbonyl, trifluoroacetyl, amino, mono- or di-alkylamino groups or an alkylene group or one or more alkyl groups which may in turn be unsubstituted or substituted by one or more hydroxy, alkoxy, hydroxyalkoxy, amino or mono- or di-alkylamino groups.

The alkyl groups and alkyl moieties such as those present in the alkoxy, alkylcarbamoyl, mono- or di-alkylamino, carbamoyl, alkylthio, oxoalkyl, alkylenedioxy, alkylamido and alkoxycarbamoyl groups mentioned herein, unless otherwise stated, are usually "lower" alkyl, that is containing from 1 to 6 particularly from 1 to 4 carbon atoms, the hydrocarbon chain being branched or straight. Preferred alkyl groups, and where relevant alkyl moieties, include methyl, ethyl, n-propyl, i-propyl, n-butyl, sec-butyl, i-butyl and t-butyl. Alkenyl and alkynyl groups mentioned in relation to formula (I) preferably have from 2 to 6 carbon atoms, most preferably from 2 to 4 carbon atoms. Acylamino groups mentioned in relation to formula (I) above preferably are of the formula —NC(O)R wherein R is an alkyl group as defined above.

Where an alkyl, alkenyl or alkynyl group, heterocyclic ring structure or moiety is described as being substituted by one or more substituents this preferably means from 1 to 3 substituents, more preferably one or two substituents.

The halogen atoms mentioned in relation to the groups $R^4$ to $R^7$ are selected from fluorine, chlorine, bromine and iodine and most preferably from bromine, chlorine and fluorine atoms.

In substituent groups of formula $$—(CH_2)_nR^7$$

n may represent 0, 1, 2, 3, or 4, preferably 0, 1, 2 or 3.

The cycloalkyl group mentioned in relation to the group $R^7$ is preferably a $C_{3-10}$ cycloalkyl group, more preferably a $C_{3-7}$ cycloalkyl group such as a cyclopropyl, cyclobutyl, cyclopentyl or cyclohexyl group. The cycloalkyl-alkyl groups within the definition —$(CH_2)_n$—$R^7$ preferably include cyclopropylmethylene, cyclopropylethylene, cyclopentylmethylene, cyclopentylethylene, cyclohexylmethylene and cyclohexylethylene. In compounds of the invention wherein the cycloalkyl group is substituted, preferred substituents include acetamido and mono- and di-alkylamino, most preferably mono- or di-ethylamino groups. The substituent group may be at any substitutable position of the cycloalkyl ring. Preferably the cycloalkyl ring is substituted at the 1-position.

When $R^7$ represents a phenyl group substituted by one or more halogen atoms or alkyl, hydroxy, alkoxy, amino, mono- or dialkyl amino, nitro, cyano or trifluoroalkyl groups, the phenyl ring may be substituted by 1, 2, 3, 4 or 5 substituents, preferably 1, 2 or 3 substituents, most preferably one or two substituents, each being independently selected from the possible substituents set out above. That is to say, the phenyl group (attached through its 1-position) may be substituted at any of the remaining positions, that is to say the 2, 3, 4, 5 or 6-positions. A phenyl group having more than one substituent may be substituted at any combination of positions. For example a phenyl group having two substituents may be substituted at the 2 and 3, 2 and 4, 2 and 5, 2 and 6, 3 and 4 or 3 and 5 positions. If the phenyl group is substituted bygone or more alkylene dioxy groups then they are preferably present on any adjacent pair of substitutable positions.

When $R^7$ represents a 3–7 membered ring in accordance with formula (I), the ring may be unsaturated or saturated and may represent for example a piperidyl, pyrrolidyl, azetidinyl, aziridyl, piperazinyl, morpholinyl, thiomorpholinyl, pyrrolyl, imidazolyl, imidazolidinyl, pyrazolinyl, indolinyl, isoindolinyl, pyridyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, quinuclidinyl, triazolyl, pyrazolyl, tetrazolyl, tetrahydrofuranyl or thienyl group, which group may be substituted or unsubstituted.

In preferred compounds of the invention $R^1$, $R^2$ and $R^3$ independently represent a group of formula $$—(CH_2)_nR^7$$

wherein $R^7$ represents a 3 to 7-membered heterocyclic ring, $R^7$ is a pyridyl, piperidyl, piperazinyl, morpholinyl, triazolyl or tetrazolyl group or hydrogen or an unsubstituted alkyl, group selected from methyl, ethyl, n-propyl, -1-propyl, n-butyl, sec-butyl and t-butyl.

In preferred compounds of the invention $R^1$ represents: hydrogen; a $C_1$–$C_4$ alkyl group; or a group of formula $$—(CH_2)_nR^7$$

wherein n is 0, 1 or 2 and $R^7$ represents phenyl, pyridyl or morpholinyl. Most preferably $R^1$ is a methyl group.

In preferred compounds of the invention $R^2$ represents: a $C_1$–$C_5$ alkyl group especially a $C_1$–$C_4$ alkyl group; a substituted $C_1$–$C_4$ alkyl group; a $C_{3-10}$ cycloalkyl group; or a group of formula $$—(CH_2)_nR^7$$

wherein n is 0, 1 or 2 and $R^7$ represents an unsubstituted or substituted phenyl or pyridyl group. Most preferably $R^2$ is an n-propyl group.

In preferred compounds of the invention $R^3$ represents: a $C_1$–$C_4$ alkyl group; a $C_{3-10}$ cycloalkyl group; or a group of formula $$—(CH_2)_nR^7$$

wherein n is 0, 1 or 2 and $R^7$ represents an unsubstituted or substituted phenyl or pyridyl group. Most preferably $R^3$ is an ethyl or n-propyl group.

For compounds of the invention wherein $R^4$ and $R^5$ together with the nitrogen atom to which they are attached form a 3 to 7-membered ring comprising a total of from 1 to 4 heteroatoms, the ring may be saturated or unsaturated and is preferably selected from a piperidyl, pyrrolidyl, azetidinyl, aziridyl, piperazinyl, [1,4]diazepan-1-yl, morpholinyl, thiomorpholinyl, pyrrolyl, pyrazolyl, imidazolyl, imidazolidinyl, pyrazolinyl, indolinyl or isoindolinyl group, said group being unsubstituted or substituted as defined above. For example, said group may be unsubstituted or substituted by an alkylene group and/or from 1 to 3 groups independently selected from $C_1$–$C_4$ alkyl, $C_2$–$C_4$ alkenyl, carbamoyl, amino, di-$C_1$–$C_4$-alkylamino, (2-hydroxyethyl)methylamino, hydroxyl, 2,2,2-trifluoroethanoyl, 2,2,2-trifluoroethyl, carbaldehyde groups and hydroxyalkyl groups, alkoxycarbonyl groups, alkoxyalkyl groups and hydroxyalkoxyalkyl groups wherein the alkyl moieties contain from 1 to 4 carbon atoms, and wherein said alkylene group may in turn be unsubstituted or substituted by one or more hydroxy, alkoxy, hydroxyalkoxy, amino or mono- or di-alkylamino groups. Typically said group is an alkylene group or from 1 to 3 groups independently selected from $C_1$–$C_4$ alkyl, $C_2$–$C_4$ alkenyl, carbamoyl, amino, di-$C_1$–$C_4$-alkylamino, (2-hydroxyethyl)methylamino, hydroxyl, 2,2,2-trifluoroethanoyl, 2,2,2-trifluoroethyl, carbaldehyde groups and hydroxyalkyl groups, alkoxycarbonyl groups, alkoxyalkyl groups and hydroxyalkoxyalkyl groups wherein the alkyl moieties contain from 1 to 4 carbon atoms.

It is to be understood that when the substituent is an alkylene group it is attached to the heterocyclic ring at any two substitutable positions which may be adjacent or not adjacent to each other. When the substitutable positions are not adjacent to each other, the alkylene group forms a bridging group. The alkylene group preferably has from 1 to 5 carbon atoms.

In preferred compounds of the invention the ring formed by $R^4$, $R^5$ and the nitrogen atom to which they are attached is a substituted or unsubstituted piperidyl, pyrrolidyl, piperazinyl, [1,4]diazepan-1-yl, morpholinyl, pyrazolyl, azetidinyl, diazabicyclo[2.2.1]hept-2-yl or hexahydropyrrolo[2,1-a]pyrazinyl group. Preferred substituent groups are one or more groups selected from $C_1$–$C_4$ alkyl, $C_2$–$C_4$ alkenyl, carbamoyl, amino, di-$C_1$–$C_4$-alkylamino, (2-hydroxyethyl) methylamino, hydroxyl, 2,2,2-trifluoroethanoyl, 2,2,2-trifluoroethyl, carbaldehyde (formyl) groups and hydroxyalkyl groups, alkoxycarbonyl groups, alkoxyalkyl groups and hydroxyalkoxyalkyl groups wherein the alkyl moieties contain from 1 to 4 carbon atoms, and $C_{1-4}$ alkylene groups wherein the alkylene group may be unsubstituted or substituted by a hydroxy group. Typically, the substituent groups are selected from $C_{1-4}$ alkyl, $C_2$–$C_4$ alkenyl, carbamoyl, amino, di-$C_1$–$C_4$-alkylamino, (2-hydroxyethyl)methylamino, hydroxyl, 2,2,2-trifluoroethanoyl, 2,2,2-trifluoroethyl, carbaldehyde (formyl) groups and hydroxyalkyl groups, alkoxycarbonyl groups, alkoxyalkyl groups and hydroxyalkoxyalkyl groups wherein the alkyl moieties contain from 1 to 4 carbon atoms.

Most preferably $R^4$ and $R^5$ together with the nitrogen atom to which they are attached represent a 4-hydroxypiperidyl, 4-carbamoylpiperidyl, 3-carbamoylpiperidyl, piperazinyl, 4-methylpiperazinyl, 4-ethylpiperazinyl, 4-formylpiperazinyl, [1,4]-diazepan-1-yl, 4-methyl-[1,4]-diazepan-1-yl, 4-(2-hydroxyethyl)piperazinyl, 4-[2-(2-hydroxyethoxy)ethyl]piperazinyl, morpholinyl, aminopyrazolyl, diazabicyclo[2.2.1]hept-2-yl, 5-methyldiazabicyclo[2.2.1]hept-2-yl, 4-ethoxycarbonylpiperazine, 4-piperazine carbaldehyde, 5-(2-hydroxyethyl)-diazabicyclo[2.2.1]hept-2-yl, 3(S)-methylpiperazinyl, 3(R)-methylpiperazinyl, (3,5)-3,5-dimethylpiperazinyl, (3R,5S)-3,5-dimethylpiperazinyl, (2R,5S)-2,5-dimethylpiperazinyl, (2S,5R)-2,5-dimethyl piperazinyl, 3-dimethylaminoazetidinyl, 3-dimethylaminomethylazetidinyl, 4-allylpiperazinyl, 4-propylpiperazinyl, hexahydropyrrolo[1,2-a]pyrazin-2-yl,(3R,5S)-3,4,5-trimethylpiperazinyl, 4-(0.2-methoxyethyl)piperazinyl, 4-(2-hydroxyethyl)[1,4]diazepan-1-yl, 4-(2-hydroxy-1-methylethyl)piperazinyl, 4-(2-hydroxy-1,1-dimethylethyl) piperazinyl, 4-(2,2,2-trifluoroethyl)piperazinyl, 4-(3-hydroxypropyl)piperazinyl, 4-(isopropyl)piperazinyl, 4-(2-ethoxyethyl)piperazinyl, 4-(2,2,2-trifluoroethanoyl) piperazinyl, 3-hydroxyazetidinyl, 3-(2-hydroxyethyl) methylaminoazetidinyl, 4-(2-hydroxyethyl)piperidyl, hexahydropyrrolo[1,2-a]pyrazinyl, 3-methylhexahydropyrrolo[1,2-a]pyrazinyl, 7-hydroxyhexahydropyrrolo[1,2-a] pyrazinyl or 5-methyl-2,5-diazabicyclo[2.2.1]heptanyl group.

For compounds of the invention wherein $R^4$ and $R^5$ independently represent hydrogen, an amidino group or an alkyl, alkenyl or alkynyl group which may be unsubstituted or substituted by one or more hydroxy, alkoxy, alkylthio, amino, mono- or di-alkylamino groups, preferably $R^4$ and $R^5$ independently represent hydrogen or a propynyl group, an amidino group or a $C_1$–$C_4$ alkyl group which is unsubstituted or substituted by a hydroxy, methyl or dimethylamino group. Most preferably $R^4$ and $R^5$ independently represent hydrogen or a methyl, ethyl, propyl, 2-hydroxyethyl, dimethylaminoethyl, propynyl, dimethylaminopropyl or amidino group.

In compounds of the invention wherein $R^5$ is a group of formula

n is preferably 0, 1, 2 or 3 and $R^7$ is preferably a group $R^8$ which represents a piperidyl, pyrrolidyl, azetidinyl, aziridyl, piperazinyl, morpholinyl, thiomorpholinyl, pyrrolyl, imidazolyl, imidazolidinyl, pyrazolinyl, indolinyl, isoindolinyl, pyridyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, quinuclidinyl, triazolyl, pyrazolyl, triazolyl, tetrazolyl or thienyl group, which group may be substituted or unsubstituted. Substituents are preferably selected from alkyl, hydroxy, alkoxy, mono- or dialkylamino, acetamide, hydroxyalkyl, alkoxyalkyl, oxoalkyl, phenyl, carbamoyl and alkylcarbamoyl groups. Methyl, hydroxy, methoxy, phenyl, ethylamino, diethylamino and acetamide groups being the most preferred substituents. Or $R^8$ represents substituted cycloalkyl or phenyl group as defined above. Most preferably $R^8$ represents a pyridyl, piperidyl, piperazinyl, morpholinyl, triazolyl, tetrazolyl, pyrrolidinyl, 1-ethylaminocyclohex-1-yl, 1-diethylaminocyclohex-1-yl, 1-ethylaminocyclohept-1-yl, 1-diethylaminocyclohept-1-yl, 3,4-dimethoxyphenyl, 1-methyl-4-phenylpiperidin-4-yl, imidazoyl, 1-methylpiperid-4-yl, tetrahydrofuranyl, 2,2,6,6,-tetramethylpiperid-4-yl, 4-hydroxypiperid-4-yl, 1-acetamidocyclohept-1-yl, 1-methyl-3-azetidinyl or 4-methylpiperazin-1-yl group.

In the most preferred compounds of the invention wherein $R^4$ and $R^5$ do not form a ring together with the nitrogen atom to which they are attached, $R^4$ represents a hydrogen atom or a methyl, ethyl, propyl or 2-hydroxyethyl group.

In the most preferred compounds of the invention wherein $R^4$ and $R^5$ do not form a ring together with the nitrogen atom to which they are attached, $R^5$ represents a 2-hydroxyethyl, 2-dimethylaminoethyl, 3-dimethylaminopropyl, amidino, propynyl, 1-pyridyl, 1-morphylinylethyl, 1-piperidylethyl, 1-morpholinylpropyl, 1-pyrrolidylethyl, 1-ethylaminocyclohexylmethyl, 1-ethylaminocycloheptylmethyl, 1-diethylaminocyclohexylmethyl, 1-diethylaminocycloheptylmethyl, 2-(3,4-dimethoxyphenyl)ethyl, 1-methyl-4-phenylpiperidin-4-ylmethyl, 1R-[1,2,4]triazol-3-yl, pyridin-4-ylmethyl,2-pyridin-2-ylethyl, 3-imidazol-1-ylpropyl, 1-methylpiperidin-4-yl, tetrahydrofuran-2-yl, tetrahydrofuran-2-ylmethyl, 2,2,6,6-tetramethylpiperidin-4-yl, 2,2,6,6-tetramethylpiperidin-4-ylmethyl, 1-acetamidocyclohept-1-ylmethyl, 1-methylazetidin-3-yl or 4-methylpiperazin-1-yl group.

In preferred compounds of the invention $R^6$ represents a fluorine, chlorine, bromine or hydrogen atom or a methyl, ethyl, n-propyl, n-butyl, methoxycarbonyl, ethoxycarbonyl, or nitro groups. Most preferably $R^6$ represents a chlorine, bromine or hydrogen atom.

Particular individual compounds of the invention include:

8-[2-Ethoxy-5-(4-ethylpiperazine-1-sulfonyl)phenyl]-6-propyl-6,9-dihydro-5H-pyrrolo[2,3-e][1,2,4]triazolo[4,3-c] pyrimidine-5-one 8-{2-Ethoxy-5-[4-(2-hydroxyethyl)piperazine-1-sulfonyl] phenyl}-6-propyl-6,9-dihydro-5H-pyrrolo[2,3-e][1,2,4] triazolo[4,3-c]pyrimidine-5-one 8-[2-Ethoxy-5-(4-methylpiperazine-1-sulfonyl)phenyl]-6-propyl-6,9-dihydro-5H-pyrrolo[2,3-e][1,2,4]triazolo[4,3-c]pyrimidine-5-one 8-[5-(4-Ethylpiperazine-1-sulfonyl)-2-propoxyphenyl]-6-propyl-6,9-dihydro-5H-pyrrolo[2,3-e][1,2,4]triazolo[4,3-c]pyrimidine-5-one 8-[5-(4-methyl-[1,4]diazepane-1-sulfonyl)-2-propoxyphenyl]-6-propyl-6,9-dihydro-5H-pyrrolo[2,3-e][1,2,4]triazolo[4,3-c]pyrimidine-5-one N-(2-Morpholin-4-ylethyl)-3-(5-oxo-6-propyl-6,9-dihydro-5H-pyrrolo[2,3-e][1,2,4]triazolo[4,3-c]pyrimidin-8-yl)-4-propoxybenzenesulfonamide 8-{5-[4-(2-hydroxyethyl)piperazine-1-sulfonyl]-2-propoxyphenyl}-6-propyl-6,9-dihydro-5H-pyrrolo[2,3-e][1,2,4]triazolo[4,3-c]pyrimidine-5-one 8-[5-(4-methylpiperazine-1-sulfonyl)-2-propoxyphenyl]-6-propyl-6,9-dihydro-5H-pyrrolo[2,3-e][1,2,4]triazolo[4,3-c]pyrimidine-5-one 7-Chloro-8-[2-ethoxy-5-(piperazine-1-sulfonyl)phenyl]-6-propyl-6,9-dihydro-5H-pyrrolo[2,3-e][1,2,4]triazolo[4,3-c]pyrimidine-5-one 7-Chloro-8-[2-ethoxy-5-(4-ethylpiperazine-1-sulfonyl)phenyl]-6-propyl-6,9-dihydro-5H-pyrrolo[2,3-e][1,2,4]triazolo[4,3-c]pyrimidine-5-one 7-Chloro-8-[2-ethoxy-5-(4-methyl-[1,4]diazepane-1-sulfonyl)phenyl]-6-propyl-6,9-dihydro-5H-pyrrolo[2,3-e][1,2,4]triazolo[4,3-c]pyrimidine-5-one 3-(7-Chloro-5-oxo-6-propyl-6,9-dihydro-5H-pyrrolo[2,3-e][1,2,4]triazolo[4,3-c]pyrimidin-8-yl)-4-ethoxy-N-(2-morpholin-4-ylethyl)benzenesulfonamide 7-Chloro-8-{2-ethoxy-5-[4-(2-hydroxyethyl)piperazine-1-sulfonyl]phenyl}-6-propyl-6,9-dihydro-5H-pyrrolo[2,3-e][1,2,4]triazolo[4,3-c]pyrimidine-5-one 7-Chloro-8-{2-ethoxy-5-[4-(3-hydroxypropyl)piperazine-1-sulfonyl]phenyl}-6-propyl-6,9-dihydro-5H-pyrrolo[2,3-e][1,2,4]triazolo[4,3-c]pyrimidine-5-one 7-Chloro-8-[2-ethoxy-5-(4-methylpiperazine-1-sulfonyl)phenyl]-6-propyl-6,9-dihydro-5H-pyrrolo[2,3-e][1,2,4]triazolo[4,3-c]pyrimidine-5-one 7-Chloro-8-[5-(3-dimethylaminomethylazetidine-1-sulfonyl)-2-ethoxyphenyl]-6-propyl-6,9-dihydro-5H-pyrrolo[2,3-e][1,2,4]triazolo[4,3-c]pyrimidine-5-one 3-(7-Chloro-5-oxo-6-propyl-6,9-dihydro-5H-pyrrolo[2,3-e][1,2,4]triazolo[4,3-c]pyrimidin-8-yl)-4-ethoxy-N-prop-2-ynylbenzenesulfonamide 8-[5-(4-Allylpiperazine-1-sulfonyl)-2-ethoxyphenyl]-7-chloro-6-propyl-6,9-dihydro-5H-pyrrolo[2,3-e][1,2,4]triazolo[4,3-c]pyrimidine-5-one 7-Chloro-8-[2-ethoxy-5-(4-isopropylpiperazine-1-sulfonyl)phenyl]-6-propyl-6,9-dihydro-5H-pyrrolo[2,3-e][1,2,4]triazolo[4,3-c]pyrimidine-5-one 7-Chloro-8-(2-ethoxy-5-[4-(2-methoxyethyl)piperazine-1-sulfonyl]phenyl)-6-propyl-6,9-dihydro-5H-pyrrolo[2,3-e][1,2,4]triazolo[4,3-c]pyrimidine-5-one 7-Chloro-8-[2-ethoxy-5-(4-propylpiperazine-1-sulfonyl)phenyl]-6-propyl-6,9-dihydro-5H-pyrrolo[2,3-e][1,2,4]triazolo[4,3-c]pyrimidine-5-one 7-Chloro-8-[5-(3-dimethylaminoazetidine-1-sulfonyl)-2-ethoxyphenyl]-6-propyl-6,9-dihydro-5H-pyrrolo[2,3-e][1,2,4]triazolo[4,3-c]pyrimidine-5-one 7-Chloro-8-{2-ethoxy-5-[4-(2-hydroxyethyl)-[1,4]diazepane-1-sulfonyl]phenyl}-6-propyl-6,9-dihydro-5H-pyrrolo[2,3-e][1,2, 4]triazolo[4,3-c]pyrimidine-5-one 7-Chloro-8-{2-ethoxy-5-[4-(2-ethoxyethyl)piperazine-1-sulfonyl] phenyl}-6-propyl-6,9-dihydro-5H-pyrrolo[2,3-e][1,2,4]triazolo[4,3-c]pyrimidine-5-one 7-Chloro-8-[5-(piperazine-1-sulfonyl)-2-propoxyphenyl]-6-propyl-6,9-dihydro-5H-pyrrolo[2,3-e][1,2,4]triazolo[4,3-c]pyrimidine-5-one 7-Chloro-8-[5-(morfolino-4-sulfonyl)-2-propoxyphenyl]-6-propyl-6,9-dihydro-5H-pyrrolo[2,3-e][1,2,4]triazolo[4,3-c]pyrimidine-5-one 7-Chloro-8-[5-(4-ethylpiperazine-1-sulfonyl)-2-propoxyphenyl]-6-propyl-6,9-dihydro-5H-pyrrolo[2,3-e][1, 2, 4]triazolo[4,3-c]pyrimidine-5-one 3-(7-Chloro-5-oxo-6-propyl-6,9-dihydro-5H-pyrrolo[2,3-e][1,2,4]triazolo[4,3-c]pyrimidin-8-yl)-N-(2-dimethylaminoethyl)-4-propoxybenzenesulfonamide 7-Chloro-8-[5-(4-methyl-[1,4]diazepane-1-sulfonyl)-2-propoxyphenyl]-6-propyl-6,9-dihydro-5S-pyrrolo[2,3-e][1, 2,4]triazolo[4,3-c]pyrimidine-5-one 3-(7-Chloro-5-oxo-6-propyl-6,9-dihydro-5H-pyrrolo[2,3-e][1,2,4]triazolo[4,3-c]pyrimidin-8-yl)-N-(2-morpholin-4-ylethyl)-4-propoxybenzenesulfonamide 7-Chloro-8-{5-[4-(2-hydroxyethyl)piperazine-sulfonyl]-2-propoxyphenyl}-6-propyl-6,9-dihydro-5H-pyrrolo[2,3-e][1,2,4]triazolo[4,3-c]pyrimidine-5-one 3-(7-Chloro-5-oxo-6-propyl-6,9-dihydro-5H-pyrrolo[2,3-e][1,2,4]triazolo[4,3-c]pyrimidin-8-yl)-N-(2-piperidin-1-yl ethyl)-4-propoxybenzenesulfonamide 3-(7-Chloro-5-oxo-6-propyl-6,9-dihydro-5H-pyrrolo[2,3-e][1,2,4]triazolo[4,3-c]pyrimidin-8-yl)-N-(3-morpholin-4-ylpropyl)-4-propoxybenzenesulfonamide 7-Chloro-8-{5-[4-(3-hydroxypropyl)piperazine-1-sulfonyl)-2-propoxyphenyl}-6-propyl-6,9-dihydro-5H-pyrrolo[2,3-e][1,2,4]triazolo[4,3-c]pyrimidine-5-one 3-(7-Chloro-5-oxo-6-propyl-6,9-dihydro-5H-pyrrolo[2,3-e][1,2,4]triazolo[4,3-c]pyrimidin-8-yl)-4-propoxy-N-(2-pyridin-2-ylethyl)benzenesulfonamide 3-(7-Chloro-5-oxo-6-propyl-6,9-dihydro-5H-pyrrolo[2,3-e][1,2,4]triazolo[4,3-c]pyrimidin-8-yl)-N-(4-methylpiperazin-1-yl)-4-propoxybenzenesulfonamide 4-[3-(7-Chloro-5-oxo-6-propyl-6,9-dihydro-5H-pyrrolo[2, 3-e][1,2,4]triazolo[4,3-c]pyrimidin-8-yl)-4-propoxybenzenesulfonyl]piperidine-1-carboxaldehyde 7-Chloro-8-{5-[4-(2-methoxyethyl)piperazine-1-sulfonyl]-2-propoxyphenyl}-6-propyl-6,9-dihydro-5H-pyrrolo[2,3-e][1,2,4]triazolo[4,3-c]pyrimidine-5-one 7-Chloro-8-[5-(4-methylpiperazine-1-sulfonyl)-2-propoxyphenyl]-6-propyl-6,9-dihydro-5H-pyrrolo[2,3-e][1, 2,4]triazolo[4,3-c]pyrimidine-5-one 7-Chloro-8-[2-propoxy-5-(4-propylpiperazine-1-sulfonyl)phenyl]-6-propyl-6,9-dihydro-5H-pyrrolo[2,3-e][1,2,4]triazolo[4,3-c]pyrimidine-5-one 3-(7-Chloro-5-oxo-6-propyl-6,9-dihydro-5H-pyrrolo[2,3-e][1,2,4]triazolo[4,3-c]pyrimidin-8-yl)-4-propoxy-N-(2,2,6,6-tetramethylpiperidin-4-yl)benzenesulfonamide 3-(7-Chloro-5-oxo-6-propyl-6,9-dihydro-5H-pyrrolo[2,3-e][1,2,4]triazolo[4,3-c]pyrimidin-8-yl)-4-propoxy-N-prop-2-ynylbenzenesulfonamide 3-(7-Chloro-5-oxo-6-propyl-6,9-dihydro-5H-pyrrolo[2,3-e][1,2,4]triazolo[4,3-c]pyrimidin-8-yl)-N-methyl-A-(1-methylpiperidin-4-yl)-4-propoxybenzenesulfonamide 7-Chloro-8-{5-[4-(2-ethoxyethyl)piperazine-1-sulfonyl]-2-propoxyphenyl}-6-propyl-6,9-dihydro-5B-pyrrolo[2,3-e][1,2,4]triazolo[4,3-c]pyrimidine-5-one 8-[5-(4-Allylpiperazine-1-sulfonyl)-2-propoxyphenyl]-7-chloro-6-propyl-6,9-dihydro-5H-pyrrolo[2,3-e][1,2,4]triazolo[4,3-c]pyrimidine-5-one 7-Chloro-8-[5-(4-isopropylpiperazine-1-sulfonyl)-2-propoxyphenyl]-6-propyl-6,9-dihydro-5H-pyrrolo[2,3-e][1, 2,4]triazolo[4,3-c]pyrimidine-5-one 7-Chloro-8-[5-(3-dimethylaminoazetidine-1-sulfonyl)-2-propoxyphenyl]-6-propyl-6,9-dihydro-5H-pyrrolo[2,3-e][1,2,4]triazolo[4,3-c]pyrimidine-5-one 3-(7-Chloro-5-oxo-6-propyl-6,9-dihydro-5H-pyrrolo[2,3-e][1,2,4]triazolo[4,3-c]pyrimidin-8-yl)-N-ethyl-4-propoxy-N-(tetrahydrofuran-2-ylmethyl)benzenesulfonamide 3-(7-Chloro-5-oxo-6-propyl-6,9-dihydro-5H-pyrrolo[2,3-e][1,2,4]triazolo[4,3-c]pyrimidin-8-yl)-N,N-dimethyl-4-propoxybenzenesulfonamide 3-(7-Chloro-5-oxo-6-propyl-6,9-dihydro-5H-pyrrolo[2,3-e][1,2,4]triazolo[4,3-c]pyrimidin-8-yl)-N-(2-hydroxyethyl)-4-propoxybenzenesulfonamide 3-(7-Chloro-5-oxo-6-propyl-6,9-dihydro-5H-pyrrolo[2,3-e][1,2,4]triazolo[4,3-c]pyrimidin-8-yl)-N-(2-dimethylaminoethyl)-N-methyl-4-propoxybenzenesulfonamide 7-Bromo-8-[2-ethoxy-5-(piperazine-1-sulfonyl)phenyl]-6-propyl-6,9-dihydro-5H-pyrrolo[2,3-e][1,2,4]triazolo[4,3-c]pyrimidine-5-one 7-Bromo-8-[2-ethoxy-5-(4-ethylpiperazine-1-sulfonyl)phenyl]-6-propyl-6,9-dihydro-5H-pyrrolo[2,3-e][1,2,4]triazolo[4,3-c]pyrimidine-5-one 3-(7-Bromo-5-oxo-6-propyl-6,9-dihydro-5H-pyrrolo[2,3-e][1,2,4]triazolo[4,3-c]pyrimidin-8-yl)-4-ethoxy-N-(2-morpholin-4-ylethyl)benzenesulfonamide 7-Bromo-8-{2-ethoxy-5-[4-(2-hydroxyethyl)piperazine-1-sulfonyl]phenyl}-6-propyl-6,9-dihydro-5H-pyrrolo[2,3-e][1,2,4]triazolo[4,3-c]pyrimidine-5-one 7-Bromo-8-[2-ethoxy-5-(4-methylpiperazine-1-sulfonyl)phenyl]-6-propyl-6,9-dihydro-5H-pyrrolo[2,3-e][1,2,4]triazolo[4,3-c]pyrimidine-5-one 7-Bromo-8-[5-(4-ethylpiperazine-1-sulfonyl)-2-propoxyphenyl]-6-propyl-6,9-dihydro-5H-pyrrolo[2,3-e][1,2,4]triazolo[4,3-c]pyrimidine-5-one 7-Bromo-8-[5-(4-methylpiperazine-1-sulfonyl)-2-propoxyphenyl]-6-propyl-6,9-dihydro-5H-pyrrolo[2,3-e][1,2,4]triazolo[4,3-c]pyrimidine-5-one 3-(7-Bromo-5-oxo-6-propyl-6,9-dihydro-5H-pyrrolo[2,3-e][1,2,4]triazolo[4,3-c]pyrimidin-8-yl)-4-propoxy-N-prop-2-ynylbenzenesulfonamide 3-(7-Bromo-5-oxo-6-propyl-6,9-dihydro-5H-pyrrolo[2,3-e][1,2,4]triazolo[4,3-c]pyrimidin-8-yl)-N,N-dimethyl-4-propoxybenzenesulfonamide 7-Bromo-8-[5-(morfolino-4-sulfonyl)-2-propoxyphenyl]-6-propyl-6,9-dihydro-5H-pyrrolo[2,3-e][1,2,4]triazolo[4,3-c]pyrimidine-5-one 7-Bromo-8-[5-(4-methyl-[1,4]diazepane-1-sulfonyl)-2-propoxyphenyl]-6-propyl-6,9-dihydro-5H-pyrrolo[2,3-e][1,2,4]triazolo[4,3-c]pyrimidine-5-one 3-(7-Bromo-5-oxo-6-propyl-6,9-dihydro-5H-pyrrolo[2,3-e][1,2,4]triazolo[4,3-c]pyrimidin-8-yl)-N-(2-morpholin-4-ylethyl)-4-propoxybenzenesulfonamide 7-Bromo-8-{5-[4-(2-ethoxyethyl)piperazine-1-sulfonyl]-2-propoxyphenyl}-6-propyl-6,9-dihydro-5B-pyrrolo[2,3-e][1,2,4]triazolo[4,3-c]pyrimidine-5-one 3-(7-Bromo-5-oxo-6-propyl-6,9-dihydro-5H-pyrrolo[2,3-e][1,2,4]triazolo[4,3-c]pyrimidin-8-yl)-4-propoxy-Al-(2,2,6,6-tetramethylpiperidin-4-yl)benzenesulfonamide 3-(7-Bromo-5-oxo-6-propyl-6,9-dihydro-5H-pyrrolo[2,3-e][1,2,4]triazolo[4,3-c]pyrimidin-8-yl)-N-methyl-N-(1-methylpiperidin-4-yl)-4-propoxybenzenesulfonamide 8-[5-(4-Allylpiperazine-1-sulfonyl)-2-propoxyphenyl]-7-bromo-6-propyl-6,9-dihydro-5H-pyrrolo[2,3-e][1,2,4]triazolo[4,3-c]pyrimidine-5-one 7-Bromo-8-[5-(4-isopropylpiperazine-1-sulfonyl)-2-propoxyphenyl]-6-propyl-6,9-dihydro-5H-pyrrolo[2,3-e][1,2,4]triazolo[4,3-c]pyrimidine-5-one 7-Bromo-8-[5-(3-dimethylaminoazetidine-1-sulfonyl)-2-propoxyphenyl]-6-propyl-6,9-dihydro-5H-pyrrolo[2,3-e][1,2,4]triazolo[4,3-c]pyrimidine-5-one 7-Bromo-8-[5-(3-dimethylaminomethylazetidine-1-sulfonyl)-2-propoxyphenyl]-6-propyl-6,9-dihydro-5H-pyrrolo[2,3-e][1,2,4]triazolo[4,3-c]pyrimidine-5-one 7-Bromo-8-(5-[4-(2-Hydroxyethyl)-[1,4]diazepane-1-sulfonyl]-2-propoxyphenyl}-6-propyl-6,9-dihydro-5H-pyrrolo[2,3-e][1,2,4]triazolo[4,3-c]pyrimidine-5-one 7-Bromo-8-[5-(3,5-dimethylpiperazine-1-sulfonyl)-2-propoxyphenyl]-6-propyl-6,9-dihydro-5H-pyrrolo[2,3-e][1,2,4]triazolo[4,3-c]pyrimidine-5-one 7-Bromo-8-{5-[4-(2-hydroxyethyl)piperazine-1-sulfonyl]-2-propoxyphenyl}-6-propyl-6,9-dihydro-5H-pyrrolo[2,3-e][1,2,4]triazolo[4,3-c]pyrimidine-5-one and 7-Bromo-8-[5-(piperazine-1-sulfonyl)-2-propoxyphenyl]-6-propyl-6,9-dihydro-5B-pyrrolo[2,3-e][1,2,4]triazolo[4,3-c]pyrimidine-5-one 7-Chloro-8-[2-ethoxy-5-((S)-hexahydropyrrolo[1,2-a]pyrazine-2-sulfonyl)phenyl]-6-propyl-6,9-dihydro-5H-pyrrolo[2,3-e][1,2,4]triazolo[4,3-c]pyrimidine-5-one 7-Chloro-8-[2-ethoxy-5-((R)-hexahydropyrrolo[1,2-a]pyrazine-2-sulfonyl)phenyl]-6-propyl-6,9-dihydro-5B-pyrrolo[2,3-e][1,2,4]triazolo[4,3-c]pyrimidine-5-one 7-Chloro-8-[2-ethoxy-5-((3R, 8aS)-3-methylhexahydropyrrolo[1,2-a]pyrazine-2-sulfonyl)phenyl]-6-propyl-6,9-dihydro-5H-pyrrolo[2,3-e][1,2,4]triazolo[4,3-c]pyrimidine-5-one 7-Chloro-8-[2-ethoxy-5-((7R, 8aS)-7-hydroxyhexahydropyrrolo[1,4,2-a]pyrazine-2-sulfonyl)phenyl]-6-propyl-6,9-dihydro-5H-pyrrolo[2,3-e][1,2,4]triazolo[4,3-c]pyrimidine-5-one 7-Chloro-8-[2-ethoxy-5-((1S, 4S)-5-methyl-2,5-diazabicyclo[2.2.1]heptane-2-sulfonyl)phenyl]-6-propyl-6,9-dihydro-5H-pyrrolo[2,3-e][1,2,4]triazolo[4,3-c]pyrimidine-5-one 7-Bromo-8-[5-((R)-hexahydropyrrolo[1,2-a]pyrazine-2-sulfonyl)-2-propoxyphenyl]-6-propyl-6,9-dihydro-5H-pyrrolo[2,3-e][1,2,4]triazolo[4,3-c]pyrimidine-5-one 7-Bromo-8-[5-((3R, 8aS)-3-methylhexahydropyrrolo[1,2-a]pyrazine-2-sulfonyl)-2-propoxyphenyl]-6-propyl-6,9-dihydro-5H-pyrrolo[2,3-e][1,2,4]triazolo[4,3-c]pyrimidine-5-one 7-Bromo-8-[5-((7R, 8aS)-7-hydroxyhexahydropyrrolo[1,2-a]pyrazine-2-sulfonyl)-2-propoxyphenyl]-6-propyl-6,9-dihydro-5H-pyrrolo[2,3-e][1,2,4]triazolo[4,3-c]pyrimidine-5-one 7-Bromo-8-[5-((1S, 4S)-5-methyl-2,5-diazabicyclo[2.2.1]heptane-2-sulfonyl)-2-propoxyphenyl]-6-propyl-6,9-dihydro-5H-pyrrolo[2,3-e][1,2,4]triazolo[4,3-c]pyrimidine-5-one 7-Iodo-8-[5-((S)-hexahydropyrrolo[1,2-a]pyrazine-2-sulfonyl)-2-propoxyphenyl]-6-propyl-6,9-dihydro-5H-pyrrolo[2,3-e][1,2,4]triazolo[4,3-c]pyrimidine-5-one 7-Iodo-8-[5-((R)-hexahydropyrrolo[1,2-a]pyrazine-2-sulfonyl)-2-propoxyphenyl]-6-propyl-6,9-dihydro-5H-pyrrolo[2,3-e][1,2,4]triazolo[4,3-c]pyrimidine-5-one 7-Iodo-8-[5-((3R, 8aS)-3-methylhexahydropyrrolo[1,2-a]pyrazine-2-sulfonyl)-2-propoxyphenyl]-6-propyl-6,9-dihydro-5H-pyrrolo[2,3-e][1,2,4]triazolo[4,3-c]pyrimidine-5-one 7-Iodo-8-[5-((7R, 8aS)-7-hydroxyhexahydropyrrolo[1,2-a]pyrazine-2-sulfonyl)-2-propoxyphenyl]-6-propyl-6,9-dihydro-5H-pyrrolo[2,3-e][1,2,4]triazolo[4,3-c]pyrimidine-5-one 7-Iodo-8-[5-((1S, 4S)-5-methyl-2,5-diazabicyclo[2.2.1]heptane-2-sulfonyl)-2-propoxyphenyl]-6-propyl-6,9-dihydro-5H-pyrrolo[2,3-e][1,2,4]triazolo[4,3-c]pyrimidine-5-one Of outstanding interest are:

7-Chloro-8-[2-ethoxy-5-(4-methyl-[1,4]diazepane-1-sulfonyl)phenyl]-6-propyl-6,9-dihydro-5H-pyrrolo[2,3-e][1,2,4]triazolo[4,3-c]pyrimidine-5-one 7-Chloro-8-{2-ethoxy-5-[4-(2-ethoxyethyl)piperazine-1-sulfonyl]phenyl}-6-propyl-6,9-dihydro-5H-pyrrolo[2,3-e][1,2,4]triazolo[4,3-c]pyrimidine-5-one 7-Chloro-8-{5-[4-(3-hydroxypropyl)piperazine-1-sulfonyl)-2-propoxyphenyl]-6-propyl-6,9-dihydro-5H-pyrrolo[2,3-e][1,2,4]triazolo[4,3-c]pyrimidine-5-one 3-(7-Chloro-5-oxo-6-propyl-6,9-dihydro-5H-pyrrolo[2,3-e][1,2,4]triazolo[4,3-c]pyrimidin-8-yl)-4-propoxy-N-(2,2,6,6-tetramethylpiperidin-4-yl)benzenesulfonamide 8-[5-(4-Allylpiperazine-1-sulfonyl)-2-propoxyphenyl]-7-chloro-6-propyl-6,9-dihydro-5H-pyrrolo[2,3-e][1,2,-]triazolo[4,3-c]pyrimidine-5-one 3-(7-Chloro-5-oxo-6-propyl-6,9-dihydro-5H-pyrrolo[2,3-e][1,2,4]triazolo[4,3-c]pyrimidin-8-yl)-N-(2-hydroxyethyl)-4-propoxybenzenesulfonamide 7-Bromo-8-[5-(4-methylpiperazine-1-sulfonyl)-2-propoxyphenyl]-6-propyl-6,9-dihydro-5H-pyrrolo[2,3-e][1,2,4]triazolo[4,3-c]pyrimidine-5-one 7-Bromo-8-{5-[4-(2-Hydroxyethyl)-[1,4]diazepane-1-sulfonyl]-2-propoxyphenyl}-6-propyl-6,9-dihydro-5H-pyrrolo[2,3-e][1,2,4]triazolo[4,3-c]pyrimidine-5-one 7-Bromo-8-{5-[4-(2-hydroxyethyl)piperazine-1-sulfonyl]-2-propoxyphenyl}-6-propyl-6,9-dihydro-5H-pyrrolo[2,3-e][1,2,4]triazolo[4,3-c]pyrimidine-5-one 7-Bromo-8-[5-(piperazine-1-sulfonyl)-2-propoxyphenyl]-6-propyl-6,9-dihydro-5H-pyrrolo[2,3-e][1,2,4]triazolo[4,3-c]pyrimidine-5-one 7-Chloro-8-[2-ethoxy-5-(S)-hexahydropyrrolo[1,2-a]pyrazine-2-sulfonyl)phenyl]-6-propyl-6,9-dihydro-5H-pyrrolo[2,3-e][1,2,4]triazolo[4,3-c]pyrimidine-5-one and 7-Chloro-8-[2-ethoxy-5-((1S, 4S)-5-methyl-2,5-diazabicyclo[2.2.1]heptane-2-sulfonyl)phenyl]-6-propyl-6,9-dihydro-5B-pyrrolo[2,3-e][1,2,4]triazolo[4,3-c]pyrimidine-5-one.

The present invention also provides processes for producing the 8-phenyl-6,9-dihydro-5H-pyrrolo[1,2,4]triazolo[4,3-c]pyrimidine-5-one derivatives of general formula (I). According to a further feature of the present invention, the 8-phenyl-6,9-dihydro-5H-pyrrolo[2,3-e][1,2,4]triazolo[4,3-c]pyrimidine-5-one derivatives of general formula (II) above are prepared by reaction of the corresponding sulphonyl chloride of formula (IV):

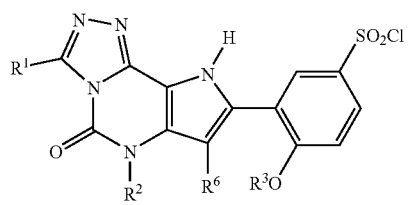

(IV)

(wherein $R^1$, $R^2$, $R^3$ and $R^6$ are as hereinbefore defined) and the corresponding amine (V):

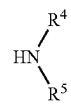

(V)

(wherein $R^4$ and $R^5$ are as hereinbefore defined) The reaction is preferably carried out in an organic solvent most preferably a polar aprotic organic solvent such as dioxane, methylene chloride or tetrahydrofuran, at a temperature from 10° C. to 40° C. and in the presence of an organic base, most preferably an amine base such as triethylamine or polymer supported morpholine. The thus obtained 8-phenyl-6,9-dihydro-5H-pyrrolo[2,3-e][1,2,4]triazolo[4,3-c]pyrimidine-5-one derivative is then preferably isolated by the conventional methods known in the art.

In the case that $R^6$ is hydrogen, the sulphonyl chloride (IV) is preferably obtained from the corresponding compound of formula (VI):

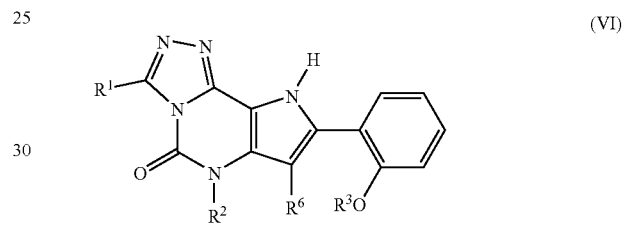

(VI)

(wherein $R^1$, $R^2$ and $R^3$ are as hereinbefore defined), by reaction with an excess of chlorosulphonic acid and optionally thionyl chloride, preferably under a nitrogen atmosphere and at a temperature from −5° C. to 10° C. and where the solvent is the same chlorosulphonic acid.

In the case that $R^6$ is a chlorine atom, the corresponding sulphonyl chloride (IV) is preferably obtained from the corresponding compound of formula (VI) by reaction with an mixture of chlorosulphonic acid and sulphuryl chloride, preferably under a nitrogen atmosphere and at a temperature from −5° C. to 10° C. and where the solvent is the same chlorosulphonic acid.

In the case that $R^6$ is a bromine atom, the desired sulphonyl chloride (IV) is preferably obtained from the corresponding sulphonyl chloride (IV) where $R^6$ is a hydrogen atom by reaction with bromine in glacial acetic acid at room temperature.

The 8-phenyl-6,9-dihydro-5H-pyrrolo[2,3-e][1,2,4]triazolo[4,3-c]pyrimidine-5-one derivatives of general formula (VI) are preferably prepared by reaction of a corresponding hydrazino derivative of formula (VII):

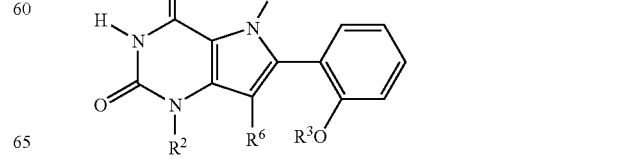

(VII)

(wherein R², R³ and R⁶ are as hereinbefore defined) with the corresponding carboxylic acid of the general formula (VIII):

R¹—COOH    (VIII)

(wherein R¹ is as hereinbefore defined) or a reactive derivative thereof. Preferred examples of a reactive derivative of the carboxylic acid (VIII) are the acid halide, orthoester or anhydride. The reaction may be carried out in a solvent, preferably a polar aprotic solvent, such as N,N-dimethylformamide, dioxane, acetone or tetrahydrofuran, in the presence of an organic base, preferably an amine base, such as triethylamine and at a temperature from 15° C. to the boiling point of the solvent.

The reaction can also be carried out in the absence of a solvent, in which case an excess of the carboxylic acid (VIII) or reactive derivative of the carboxylic acid (VIII) is used and the mixture is heated at a temperature from 40° C. to its boiling point. The thus obtained 8-phenyl-6,9-dihydro-5H-pyrrolo[2,3-e][1,2,4]triazolo[4,3-c]pyrimidine-5-one derivative is preferably then isolated by conventional methods known in the art.

The hydrazinopurines of general formula (VII) are preferably obtained by reaction of the 6-thioxopurines of the general formula (IX):

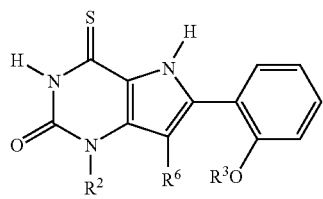

(wherein R², R³ and R⁶ are as hereinbefore defined) with hydrazine hydrate at a temperature from 80 to 150° C.

The 6-thioxo derivatives of general formula (IX) are preferably obtained by reaction of the 6-phenylpyrrolopyrimidinedione of general formula (X):

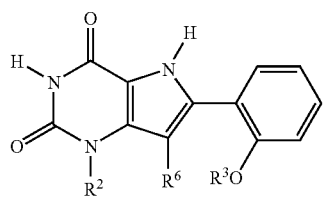

(wherein R², R³ and R⁶ are as hereinbefore defined) with phosphorus pentasulphide or Lawesson's reagent (2,4-bis(4-methoxyphenyl)-1,3-dithia-2,4-diphosphetane-2,4-disulphide). The reaction is preferably carried out in a solvent, such as benzene, toluene, dioxane or pyridine, at a temperature from 40° C. to the boiling point of the solvent.

The 6-phenylpyrrolopyrimidinedione derivatives of general formula (X) are preferably prepared by a process comprising reaction of the corresponding 6-methyl-5-nitrouracil of formula (XI):

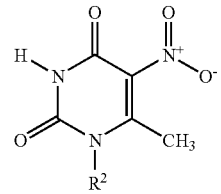

(wherein R² is as hereinbefore defined), and the corresponding benzaldehyde of formula (XII)

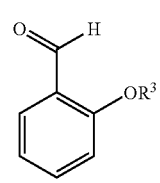

(wherein R³ is as hereinbefore defined), followed by reductive cyclization of the resulting 5-nitro-6-styryluracils by methods known per se, e.g. C. E. Muller et al., *J. Med. Chem.* 1994, 37, 1526–1534 and references cited therein.

Substitutions other than chlorine or bromine atoms at R⁶ can be introduced by reaction of the corresponding compound of general formula (II), (IV) or (VI) wherein R⁶ is a hydrogen atom or a suitably protected version of them with an appropriate electrophile.

According to a further feature of the present invention, the 8-phenyl-6,9-dihydro-5H-pyrrolo[3,2-e][1,2,4]triazolo[4,3-c]pyrimidine-5-one derivatives of general formula (III) above are prepared by reaction of a corresponding hydrazino derivative of formula (XIII):

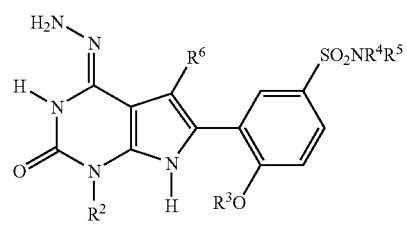

(wherein R², R³, R⁴, R⁵ and R⁶ are as hereinbefore defined) with the corresponding carboxylic acid of the general formula (VIII):

R¹—COOH    (VIII)

(wherein R¹ is as hereinbefore defined) or a reactive derivative thereof. Preferred examples of a reactive derivative of the carboxylic acid (VIII) are the acid halide, orthoester or anhydride. The reaction may be carried out in a solvent, preferably a polar aprotic solvent, such as N,N-dimethylformamide, dioxane, acetone or tetrahydrofuran, in the presence of an organic base, preferably an amine base, such as triethylamine and at a temperature from 15° C. to the boiling point of the solvent.

The reaction can also be carried out in the absence of a solvent, in which case an excess of the carboxylic acid (VIII)

or reactive derivative of the carboxylic acid (VIII) is used and the mixture is heated at a temperature from 40° C. to its boiling point. The thus obtained 8-phenyl-6,9-dihydro-5H-pyrrolo[3,2-e][1,2,4]triazolo[4,3-c]pyrimidine-5-one derivative is then isolated by usual methods known in the art.

The hydrazinopurines of general formula (XIII) are preferably obtained by reaction of the 6-thioxopurines of the general formula (XIV):

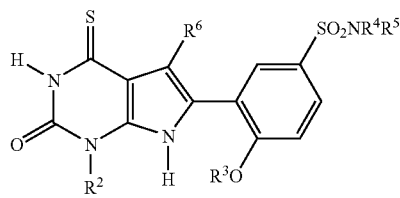
(XIV)

(wherein $R^2$, $R^3$, $R^4$, $R^5$ and $R^6$ are as hereinbefore defined) with hydrazine hydrate at a temperature from 80 to 150° C.

The 6-thioxo derivatives of general formula (XIV) are preferably obtained by reaction of the 6-phenylpyrrolopyrimidinedione of general formula (XV):

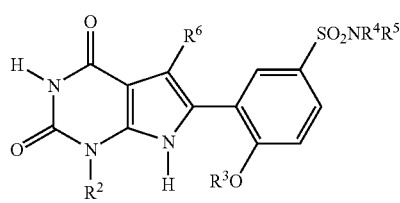
(XV)

(wherein $R^2$, $R^3$, $R^4$, $R^5$ and $R^6$ are as hereinbefore defined) with phosphorus pentasulphide or Lawesson's reagent (2,4-bis(4-methoxyphenyl)-1,3-dithia-2,4-diphosphetane-2,4-disulphide). The reaction is preferably carried out in a solvent, such as benzene, toluene, dioxane or pyridine, at a temperature from 40° C. to the boiling point of the solvent.

The 6-phenyl-1,7-dihydropyrrolo[2,3-d]pyrimidine-2,4-dione derivatives of general formula (XV) are preferably prepared by condensation of the corresponding 6-aminouracil of formula (XVI):

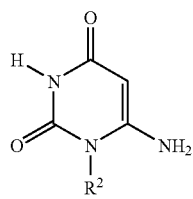
(XVI)

(wherein $R^2$ is as hereinbefore defined), with the corresponding bromoacetophenones of formula (XVII):

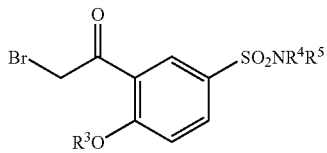
(XVII)

(wherein $R^3$, $R^4$ and $R^5$ are as hereinbefore defined), by methods known per se, e.g. C. W. Noell et al., *J. Heterocycl. Chem.* 1964, 1, 34–41, and H. Ogura et al., *Chem. Pharm. Bull.* 1972, 6, 404–408.

The 6-aminouracils of general formula (XVI) can be prepared from the corresponding N-substituted ureas by methods known per se, e.g. V. Papesch et al., *J. Org. Chem.* 1951, 16, 1879–90.

The bromoacetophenones (XVII) can be prepared from the corresponding 2-alkoxyacetophenones (XVIII):

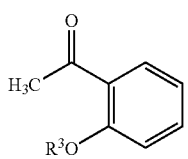
(XVIII)

(wherein $R^3$ is as hereinbefore defined), by chlorosulphonylation, reaction with the corresponding amine (V):

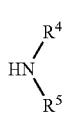
(V)

and further bromination of the resulting compound by methods known per se.

When the defined groups $R^1$ to $R^6$ are susceptible to chemical reaction under the conditions of the hereinbefore described processes or are incompatible with said processes, alternative processes can be readily carried out utilising organic synthetic chemistry methods to, for example, protect functional groups and finally eliminate protecting groups. Substitutions at $R^6$ can be introduced by reaction of the corresponding compound of general formula (III) wherein $R^6$ is a hydrogen atom or a suitably protected version of them with an appropriate electrophile.

The 8-phenyl-6,9-dihydro-5H-pyrrolo[1,2,4]triazolo[4,3-c]pyrimidine-5-one derivatives of formula (I) can be converted by methods known per se into pharmaceutically acceptable salts, preferably acid addition salts by treatment with organic or inorganic acids such as fumaric, tartaric, succinic or hydrochloric acid. Also 8-phenyl-6,9-dihydro-5H-pyrrolo[1,2,4]triazolo[4,3-c]pyrimidine-5-one derivatives of formula (I) in which there is the presence of an acidic group, may be converted into pharmacologically acceptable salts by reaction with an alkali metal hydroxide or an organic base such as sodium or potassium hydroxide. The acid or alkali addition salts so formed may be interchanged with suitable pharmaceutically acceptable counter ions using process known per se.

The cyclic GMP specific phosphodiesterase (PEE 5) was isolated from human platelet lysates by ion exchange chromatography using a Mono-Q column. The enzyme activity was determined using 0.25 mM [3H]-cyclic GMP as substrate. The purification of the enzyme and the assessment of the PDE 5 inhibitory activity of our compounds were performed essentially as described by Gristwood et al., *Br. J. Pharmacol.* 1992, 105, 985–991.

The results are shown in Table 1.

TABLE 1

| Example | IC$_{50}$ PDE5 (nM) |
|---|---|
| 11 | 0.099 |
| 24 | 0.042 |
| 34 | 0.22 |
| 41 | 0.17 |
| 45 | 0.21 |
| 50 | 0.15 |
| 58 | 0.3 |
| 71 | 0.12 |
| 73 | 0.33 |
| 74 | 0.25 |
| 75 | 0.19 |
| 79 | 0.19 |

It can be seen from Table 1 that the compounds of formula (I) are potent inhibitors of cyclic GMP specific phosphodiesterase (PDE 5). Preferred 8-phenyl-6,9-dihydro-5H-pyrrolo[2,3-e][1,2,4]triazolo[4,3-c]pyrimidine-5-one and 8-phenyl-6,9-dihydro-5H-pyrrolo[3,2-e][1,2,4]triazolo[4,3-c]pyrimidine-5-one derivatives of the invention possess an IC$_{50}$ value for the inhibition of PDE 5 (determined as defined above) of less than 10 nM, preferably less than 5 nM and most preferably less than 1 nM. The 8-phenyl-6,9-dihydro-5H-pyrrolo[2,3-e][1,2,4]triazolo[4,3-c]pyrimidine-5-one and 8-phenyl-6,9-dihydro-5H-pyrrolo[3,2-e][1,2,4]triazolo[4,3-c]pyrimidine-5-one derivatives of the invention are useful in the treatment of stable, unstable and variant angina, hypertension, pulmonary hypertension, congestive heart failure, renal failure, atherosclerosis, conditions of reduced blood vessel potency, peripheral vascular disease, following Examples (including Preparation Examples (Preparations 1–8)) which do not limit the scope of the invention in any way.

$^1$H Nuclear Magnetic Resonance Spectra were recorded on a Varian Gemini 300 spectrometer. Low Resolution Mass Spectra (m/z) were recorded on a Micromass ZMD mass spectrometer using ESI ionization. Melting points were recorded using a Perkin Elmer DSC-7 apparatus. The chromatographic separations were obtained using a Waters 2690 system equipped with a Symmetry C18 (2.1×10 mm, 3.5 mM) column. The mobile phase was formic acid (0.4 mL), ammonia (0.1 mL), methanol (500 mL) and acetonitrile (500 mL) (B) and formic acid (0.46 mL), ammonia (0.115 mL) and water (1000 mL) (A): initially from 0% to 95% of B in 20 min, and then 4 min. with 95% of B. The reequilibration time between two injections was 5 min. The flow rate was 0.4 mL/min. The injection volume was 5 mL. Diode array chromatograms were collected at 210 nM.

PREPARATION EXAMPLES

Preparation 1

8-(2-ethoxyphenyl)-6-propyl-6,9-dihydro-5H-pyrrolo[2,3-e][1,2,4]triazolo[4,3-c]pyrimidine-5-one a) A solution of 6-methyl-5-nitro-1-propyl-1H-pyrimidine-2,4-dione (8.23 g, 38.6 mmol), 2-ethoxy benzaldehyde (8.1 mL, 57.92 mmol) and piperidine (5.73 mL, 57.92 mmol) in ethanol (180 mL) with 3A molecular sieves (12.8 g) was refluxed for 4 hours. The resulting suspension was diluted with dichloromethane (100 mL), filtrated and the filtrates were evaporated under reduced pressure. The residue was suspended in water (100 mL) and acetic acid was added until pH was slightly acidic. The aqueous suspension was partitioned between dichloromethane and brine, then the organic phase was separated, washed with water, dried (MgSO$_4$) and evaporated under reduced pressure. The residue was vascular disorders (e.g. Raynaud's disease), stroke, bronchitis, chronic asthma, allergic asthma, allergic rhinitis, glaucoma, male erectile dysfunction, female sexual dysfunction and diseases characterised by disorders of gut motility, e.g. irritable bowel syndrome.

Accordingly, the B-phenyl-6,9-dihydro-5B-pyrrolo[2,3-e][1,2,4]triazolo[4,3-c]pyrimidine-5-one and 8-phenyl-6,9-dihydro-5H-pyrrolo[3,2-e][1,2,4]triazolo[4,3-c]pyrimidine-5-one derivatives of the invention and pharmaceutically acceptable salts thereof, and pharmaceutical compositions comprising such compound and/or salts thereof, may be used in a method of treatment of disorders of the human body which comprises administering to a patient requiring such treatment an effective amount of a 8-phenyl-6,9-dihydro-5.-pyrrolo[2,3-e][1,2,4]triazolo[4,3-c]pyrimidine-5-one or 8-phenyl-6,9-dihydro-5H-pyrrolo[3,2-e][1,2,4]triazolo[4,3-c]pyrimidine-5-one derivative of the invention or a pharmaceutically acceptable salt thereof.

The present invention also provides pharmaceutical compositions which comprise, as an active ingredient, at least a 8-phenyl-6,9-dihydro-5H-pyrrolo[1,2,4]triazolo[4,3-c]pyrimidine-5-one derivative of formula (I) or a pharmaceutically acceptable salt thereof in association with a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application. Preferably the compositions are made up in a form suitable for oral, topical, nasal, rectal, percutaneous or injectable administration.

The pharmaceutically acceptable excipients which are admixed with the active compound, or salts of such compound, to form the compositions of this invention are well-known per se and the actual excipients used depend inter alia on the intended method of administering the compositions.

Compositions of this invention are preferably adapted for injectable and per os administration. In this case, the compositions for oral administration may take the form of tablets, retard tablets, sublingual tablets, capsules, inhalation aerosols, inhalation solutions, dry powder inhalation, or liquid preparations, such as mixtures, elixirs, syrups or suspensions, all containing the compound of the invention; such preparations may be made by methods well-known in the art.

The diluents which may be used in the preparation of the compositions include those liquid and solid diluents which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Effective doses are normally in the range of 10–600 mg of active ingredient per day. Daily dosage may be administered in one or more treatments, preferably from 1 to 4 treatments, per day.

The syntheses of the compounds of the invention and of the intermediates for use therein are illustrated by the triturated with ethyl ether and the precipitate collected by filtration and dried under vacuum to yield 6-[(E)-2-(2-ethoxyphenyl)vinyl]-5-nitro-1-propyl-1H-pyrimidine-2,4-dione (10.24 g, 77%) as a yellow solid.

d($CDCl_3$): 0.98 (t, 3H), 1.48 (t, 3H), 1.77 (m, 2H), 3.86 (t, 2H), 4.11 (q, 2H), 6.95 (m, 3H), 7.36 (m, 3H).

b) To a stirred solution of the above compound (10.17 g, 29.44 mmol) in formic acid (271 mL) was slowly added sodium dithionite (29.73 g, 170.7 mmol) and the mixture was refluxed overnight. The resulting solution was cooled to room temperature and poured into water (1.5 L). The precipitate was collected-by filtration and washed with water and ethyl ether, then dried under vacuum to yield 6-(2-Ethoxyphenyl)-1-propyl-1,5-dihydropyrrolo[3,2-d]pyrimidine-2,4-dione (7.73 g, 84%) as a white solid.

d(DMSO-d6): 0.96 (t, 3H), 1.42 (t, 3H), 1.73 (m, 2H), 3.80 (t, 2H), 4.13 (q, 2H), 6.68 (s, 1H), 7.05 (t, 1H), 7.15 (d, 1H), 7.32 (t, 1H), 7.81 (d, 1H), 10.86 (bs, 1H), 11.96 (bs, 1H).

c) Phosphorus pentasulphide (4.24 g, 19.14 mmol) was added portionwise to a stirred suspension of the above compound (4 g, 12.76 mmol) in pyridine (60 mL) and the resulting mixture stirred under reflux for 3 hours, then evaporated under reduced pressure. The residue was triturated with water and the precipitate collected by filtration and dried under vacuum to yield 6-(2-ethoxy phenyl)-1-propyl-4-thioxo-1,3,4,5-tetrahydropyrrolo[3,2-d]pyrimidin-2-one (4 g, 95%) as a yellow solid.

d) A stirred mixture of the above compound (4.2 g, 12.76 mmol) and hydrazine monohydrate (43 mL) was heated to 130° C. for 2 hours. The resulting mixture was cooled and the precipitate collected by filtration and washed with water and ethyl ether, then dried under vacuum to yield 6-(2-ethoxyphenyl)-4-hydrazono-1-propyl-1,3,4,5-tetrahydropyrrolo[3,2-d]pyrimidin-2-one (3.17 g, 76%) as an off-white solid.

e) A stirred mixture of the above compound (3.17 g, 9.68 mmol) and formic acid (32 mL) was heated under reflux for 2 hours. The resulting solution was concentrated under vacuum and the residue partitioned between dichloromethane and aqueous sodium bicarbonate solution, then the organic phase separated, washed with water, dried ($MgSO_4$) and evaporated under reduced pressure to yield 8-(2-ethoxy phenyl)-6-propyl-6,9-dihydro-5H-pyrrolo[2,3-e][1,2,4]triazolo[4,3-c]pyrimidine-5-one (3.11 g, 95%) as a yellowish solid.

d($CDCl_3$): 1.05 (t, 3H), 1.65 (t, 3H), 1.91 (m, 2H), 4.16 (t, 2H), 4.34 (q, 2H), 6.58 (s, 1H), 7.06 (m, 2H), 7.35 (m, 1H), 7.74 (d, 1H), 8.97 (s, 1H), 10.79 (bs, 1H).

Preparation 2

4-Ethoxy-3-(5-oxo-6-propyl-6,9-dihydro-5H-pyrrolo[2,3-e][1,2,4]triazolo[4,3-c]pyrimidin-8-yl)benzenesulfonyl chloride The title compound of Preparation 1 (2 g, 5.92 mmol) was added portionwise to a mixture of chlorosulfonic acid (10 mL) and thionyl chloride (1 mL) and stirred at 0° C. for 45 minutes. The reaction mixture was carefully poured into stirred ice-water and the aqueous suspension was partitioned between dichloromethane and brine, then the organic phase was separated, washed with water, dried ($MgSO_4$) and evaporated under reduced pressure to yield the title product (2.5 g, 90%) as a white solid.

Preparation 3

3-(7-Chloro-5-oxo-6-propyl-6,9-dihydro-5B-pyrrolo[2,3-e][1,2,4]triazolo[4,3-c]pyrimidin-8-yl)-4-ethoxybenzene sulfonyl chloride The title compound of Preparation 1 (0.7 g, 2.07 mmol) was added portionwise to a mixture of chlorosulfonic acid (3.5 mL) and sulfuryl chloride (1.75 mL) and stirred at 0° C. for 2 hours. The reaction mixture was carefully poured into stirred ice-water and the aqueous suspension was partitioned between dichloromethane and brine, then the organic phase was separated, washed with water, dried ($MgSO_4$) and evaporated under reduced pressure to yield the title compound (0.9 g, 93%) as a yellowish solid.

d($CDCl_3$): 1.05 (t, 3H), 1.38 (t, 3H), 1.90 (m, 2H), 4.21 (q, 2H), 4.48 (t, 3H), 7.18 (d, 1H), 8.12 (dd, 1H), 8.37 (d, 1H), 8.81 (s, 1H), 12.98 (bs, 1H).

Preparation 4

3-(7-Bromo-5-oxo-6-propyl-6,9-dihydro-5H-pyrrolo[2,3-e][1,2,4]triazolo[4,3-c]pyrimidin-8-yl)-4-ethoxybenzene sulfonyl chloride To a solution of the title compound of Preparation 2 (0.24 g, 0.55 mmol) in glacial acetic acid (5 mL), was slowly added bromine (0.033 mL, 0.64 mmol) and the mixture was stirred at room temperature for 1 hour. Then the reaction mixture was poured into ice-water and partitioned between dichloromethane and brine, the organic phase was separated, dried ($MgSO_4$) and evaporated under reduced pressure to yield the title product (0.21 g, 75%).

Preparation 5

B-(2-Propoxyphenyl)-6-propyl-6,9-dihydro-5B-pyrrolo[2,3-e][1,2,4]triazolo[4,3-c]pyrimidine-5-one Obtained as a white solid (50% overall) from 6-methyl-5-nitro-1-propyl-1H-pyrimidine-2,4-dione and 2-propoxybenzaldehyde following the procedure described in Preparation 1.

d(DMSO-d6): 1.02 (m, 6H), 1.82 (m, 4H), 4.03 (m, 4H), 6.91 (s, 1H), 7.10 (m, 2H), 7.35 (t, 1H), 7.91 (d, 1H), 9.18 (s, 1H), 12.58 (bs, 1H).

Preparation 6

3-(5-Oxo-6-propyl-6,9-dihydro-5B-pyrrolo[2,3-e][1,2,4]triazolo[4,3-c]pyrimidin-8-yl)-4-propoxybenzenesulfonyl chloride Obtained as a white solid (80%) from the title compound of Preparation 5, using the procedure described in Preparation 2.

d(CDCl$_3$): 1.10 (m, 6H), 2.03 (m, 4H), 4.21 (t, 2H), 4.52 (t, 2H), 6.75 (s, 1H), 7.22 (d, 1H), 8.05 (dd, 1H), 8.38 (d, 1H), 8.88 (s, 1H), 12.50 (bs, 1H).

Preparation 7

3-(7-Chloro-5-oxo-6-propyl-6,9-dihydro-5S-pyrrolo[2,3-e][1,2,4]triazolo[4,3-c]pyrimidin-8-yl)-4-propoxybenzene sulfonyl chloride Obtained as a yellowish solid (90%) from the title compound of Preparation 5, using the procedure described in Preparation 3.

d(DMSO-d6): 0.93 (m, 6H), 1.70 (m, 4H), 3.99 (t, 2H), 4.35 (t, 2H), 7.17 (d, 1H), 7.60 (d, 1H), 7.65 (dd, 1H), 9.27 (s, 1H), 13.2 (bs, 1H).

Preparation 8

3-(7-Bromo-5-oxo-6-propyl-6,9-dihydro-5B-pyrrolo[2,3-e][1,2,4]triazolo[4,3-c]pyrimidin-8-yl)-4-propoxybenzenesulfonyl chloride Obtained as a white solid (92%) from the title compound of Preparation 6, using the procedure described in Preparation 4.

d(CDCl$_3$): 0.98 (t, 3H), 1.10 (t, 3H), 1.88 (m, 4H), 4.15 (t, 2H), 4.58 (t, 2H), 7.21 (d, 1H), 8.12 (dd, 1H), 8.30 (d, 1H), 8.88 (s, 1H), 12.85 (bs, 1H).

Preparation 9

3-(7-Iodo-5-oxo-6-propyl-6,9-dihydro-5B-pyrrolo[2,3-e][1,2,4]triazolo[4,3-c]pyrimidin-8-yl)-4-propoxybenzenesulfonyl chloride To a solution of the title compound of Preparation 6 (0.77 g, 1.71 mmol) in glacial acetic acid (5 mL), was slowly added iodine monochloride (0.18 mL, 3.42 mmol) and the mixture was stirred at room temperature for 2 hours. Then the reaction mixture was poured into ice-water and partitioned between dichloromethane and brine, the organic phase was separated, dried (MgSO$_4$) and evaporated under reduced pressure to yield the title product (0.83 g, 84%).

d(CDCl$_3$): 0.98 (t, 3H), 1.10 (t, 3H), 1.89 (m, 4H), 4.18 (t, 2H), 4.60 (t, 2H), 7.22 (d, 1H), 8.16 (dd, 1H), 8.22 (d, 1H), 8.82 (s, 1H), 12.60 (bs, 1H).

EXAMPLES

TABLE 2

| Example No | $R^1$ | $R^2$ | $R^3$ | $R^6$ | $NR^4R^5$ |
|---|---|---|---|---|---|
| 1 | H | nPr | Et | H | piperazine-N-ethyl |
| 2 | H | nPr | Et | H | piperazine-N-CH$_2$CH$_2$OH |
| 3 | H | nPr | Et | H | piperazine-N-methyl |
| 4 | H | nPr | nPr | H | piperazine-N-ethyl |
| 5 | H | nPr | nPr | H | homopiperazine-N-methyl |
| 6 | H | nPr | nPr | H | HN-CH$_2$CH$_2$-morpholine |
| 7 | H | nPr | nPr | H | piperazine-N-CH$_2$CH$_2$OH |
| 8 | H | nPr | nPr | H | piperazine-N-methyl |
| 9 | H | nPr | Et | Cl | piperazine-NH |
| 10 | H | nPr | Et | Cl | piperazine-N-ethyl |
| 11 | H | nPr | Et | Cl | homopiperazine-N-methyl |
| 12 | H | nPr | Et | Cl | HN-CH$_2$CH$_2$-morpholine |

TABLE 2-continued
(I)
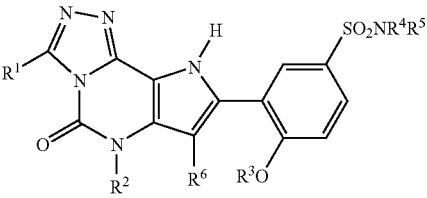
| Example No | R¹ | R² | R³ | R⁶ | NR⁴R⁵ |
|---|---|---|---|---|---|
| 13 | H | nPr | Et | Cl | 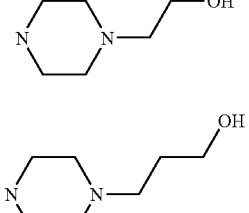 |
| 14 | H | nPr | Et | Cl | 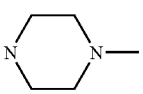 |
| 15 | H | nPr | Et | Cl | 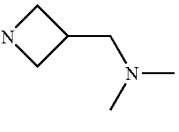 |
| 16 | H | nPr | Et | Cl |  |
| 17 | H | nPr | Et | Cl | 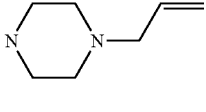 |
| 18 | H | nPr | Et | Cl | 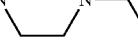 |
| 19 | H | nPr | Et | Cl | 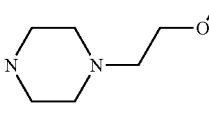 |
| 20 | H | nPr | Et | Cl | 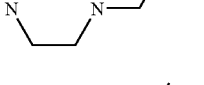 |
| 21 | H | nPr | Et | Cl |  |
| 22 | H | nPr | Et | Cl | 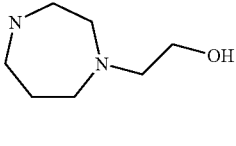 |
| 23 | H | nPr | Et | Cl | 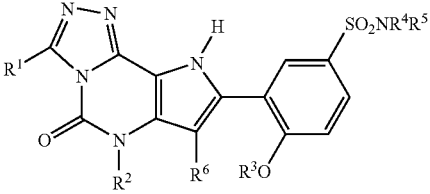 |
| 24 | H | nPr | Et | Cl | 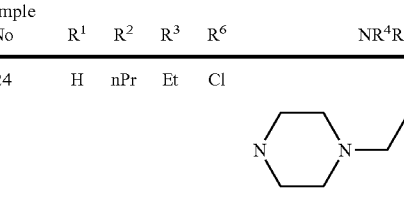 |
| 25 | H | nPr | nPr | Cl | 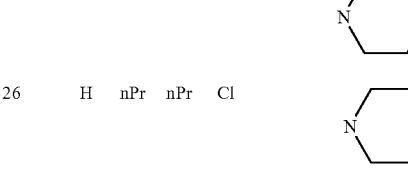 |
| 26 | H | nPr | nPr | Cl | 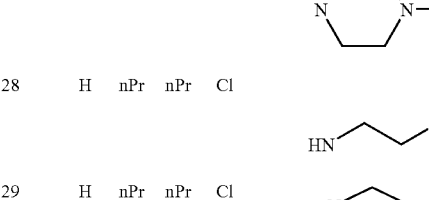 |
| 27 | H | nPr | nPr | Cl | 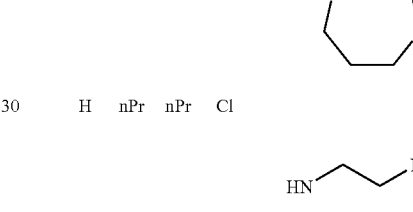 |
| 28 | H | nPr | nPr | Cl | 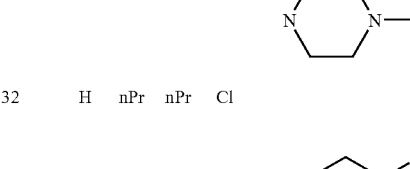 |
| 29 | H | nPr | nPr | Cl | 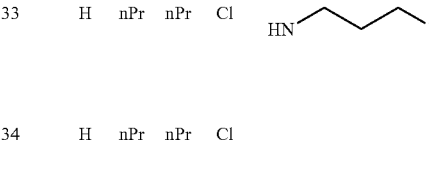 |
| 30 | H | nPr | nPr | Cl |  |
| 31 | H | nPr | nPr | Cl |  |
| 32 | H | nPr | nPr | Cl | |
| 33 | H | nPr | nPr | Cl | |
| 34 | H | nPr | nPr | Cl | |

TABLE 2-continued (I)

| Example No | R¹ | R² | R³ | R⁶ | NR⁴R⁵ |
|---|---|---|---|---|---|
| 35 | H | nPr | nPr | Cl | HN-CH₂CH₂-(2-pyridyl) |
| 36 | H | nPr | nPr | Cl | HN-N(4-methylpiperazin-1-yl) |
| 37 | H | nPr | nPr | Cl | 4-formylpiperazin-1-yl |
| 38 | H | nPr | nPr | Cl | 4-(2-methoxyethyl)piperazin-1-yl |
| 39 | H | nPr | nPr | Cl | 4-methylpiperazin-1-yl |
| 40 | H | nPr | nPr | Cl | 4-propylpiperazin-1-yl |
| 41 | H | nPr | nPr | Cl | HN-(2,2,6,6-tetramethylpiperidin-4-yl) |
| 42 | H | nPr | nPr | Cl | HN-CH₂-C≡CH |
| 43 | H | nPr | nPr | Cl | N-methyl-N-(1-methylpiperidin-4-yl) |
| 44 | H | nPr | nPr | Cl | 4-(2-ethoxyethyl)piperazin-1-yl |
| 45 | H | nPr | nPr | Cl | 4-allylpiperazin-1-yl |
| 46 | H | nPr | nPr | Cl | 4-isopropylpiperazin-1-yl |
| 47 | H | nPr | nPr | Cl | 3-(dimethylamino)azetidin-1-yl |
| 48 | H | nPr | nPr | Cl | N-ethyl-N-(tetrahydrofuran-2-yl) |
| 49 | H | nPr | nPr | Cl | N,N-dimethyl |
| 50 | H | nPr | nPr | Cl | HN-CH₂CH₂OH |
| 51 | H | nPr | nPr | Cl | N-methyl-N-(2-dimethylaminoethyl) |
| 52 | H | nPr | Et | Br | piperazin-1-yl |
| 53 | H | nPr | Et | Br | 4-ethylpiperazin-1-yl |
| 54 | H | nPr | Et | Br | HN-CH₂CH₂-morpholin-4-yl |
| 55 | H | nPr | Et | Br | 4-(2-hydroxyethyl)piperazin-1-yl |
| 56 | H | nPr | Et | Br | 4-methylpiperazin-1-yl |
| 57 | H | nPr | nPr | Br | 4-ethylpiperazin-1-yl |
| 58 | H | nPr | nPr | Br | 4-methylpiperazin-1-yl |

TABLE 2-continued (I)

| Example No | R¹ | R² | R³ | R⁶ | NR⁴R⁵ |
|---|---|---|---|---|---|
| 59 | H | nPr | nPr | Br | HN-CH₂-C≡CH |
| 60 | H | nPr | nPr | Br | dimethylamino |
| 61 | H | nPr | nPr | Br | morpholino |
| 62 | H | nPr | nPr | Br | 4-methyl-1,4-diazepan-1-yl |
| 63 | H | nPr | nPr | Br | HN-CH₂CH₂-morpholino |
| 64 | H | nPr | nPr | Br | 4-(2-methoxyethyl)piperazin-1-yl |
| 65 | H | nPr | nPr | Br | 4-amino-2,2,6,6-tetramethylpiperidine |
| 66 | H | nPr | nPr | Br | 1-methyl-4-(methylamino)piperidine |
| 67 | H | nPr | nPr | Br | 4-allylpiperazin-1-yl |
| 68 | H | nPr | nPr | Br | 4-isopropylpiperazin-1-yl |
| 69 | H | nPr | nPr | Br | 3-(dimethylamino)azetidin-1-yl |
| 70 | H | nPr | nPr | Br | 3-((dimethylamino)methyl)azetidin-1-yl |
| 71 | H | nPr | nPr | Br | 4-(2-hydroxyethyl)-1,4-diazepan-1-yl |
| 72 | H | nPr | nPr | Br | 3,5-dimethylpiperazin-1-yl |
| 73 | H | nPr | nPr | Br | 4-(2-hydroxyethyl)piperazin-1-yl |
| 74 | H | nPr | nPr | Br | piperazin-1-yl |
| 75 | H | nPr | Et | Cl | octahydroindolizine |
| 76 | H | nPr | Et | Cl | octahydropyrrolo[1,2-a]pyrazine |
| 77 | H | nPr | Et | Cl | methyl-octahydropyrrolo[1,2-a]pyrazine |
| 78 | H | nPr | Et | Cl | hydroxy-octahydropyrrolo[1,2-a]pyrazine |
| 79 | H | nPr | Et | Cl | methyl-diazabicyclo |

TABLE 2-continued

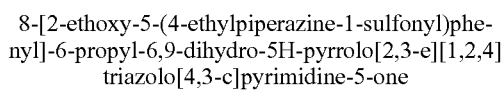

| Example No | R¹ | R² | R³ | R⁶ | NR⁴R⁵ |
|---|---|---|---|---|---|
| 80 | H | nPr | nPr | Br | 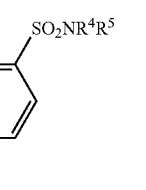 |
| 81 | H | nPr | nPr | Br | 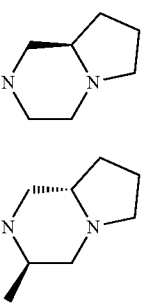 |
| 82 | H | nPr | nPr | Br | 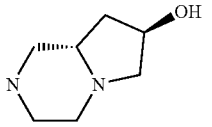 |
| 83 | H | nPr | nPr | Br | 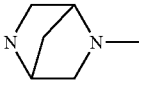 |
| 84 | H | nPr | nPr | I | 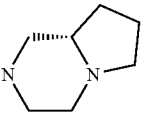 |
| 85 | H | nPr | nPr | I | 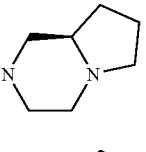 |
| 86 | H | nPr | nPr | I | 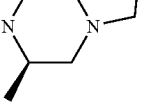 |
| 87 | H | nPr | nPr | I | 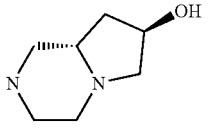 |
| 88 | H | nPr | nPr | I | 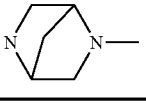 |

Example 1

8-[2-ethoxy-5-(4-ethylpiperazine-1-sulfonyl)phenyl]-6-propyl-6,9-dihydro-5H-pyrrolo[2,3-e][1,2,4]triazolo[4,3-c]pyrimidine-5-one To a mixture of the title compound of Preparation 2 (50 mg, 0.115 mmol) and polymer bound morpholine (85 mg, 2.75 mmol/g based on nitrogen analysis) in dichloromethane (3 mL) was added 1-ethylpiperazine (0.016 mL, 0.126 mmol) and the resulting mixture was stirred at room temperature overnight. The reaction mixture was filtered and the filtrate was evaporated under reduced pressure. The residue was triturated with diethyl ether and the precipitate was collected by filtration and dried under vacuum to yield the title compound (49 mg, 83%) as a white solid.

ESI/MS m/e: 514 ([M+H]$^+$, $C_{24}H_{31}N_7O_4S$)

Retention Time (min.): 11.6

Examples 2–3

The compounds of this invention were synthesized from the title compound of Preparation 2 following the procedure of example 1 and using the corresponding reactant respectively. The ESI/MS data, HPLC retention times and yields are summarised in Table 3.

TABLE 3

| Example | Molecular Formula | ESI/MS m/e [M + H]$^+$ | Retention Time (min.) | Yield % |
|---|---|---|---|---|
| 2 | $C_{24}H_{31}N_7O_5S$ | 530 | 11.6 | 75 |
| 3 | $C_{23}H_{29}N_7O_4S$ | 500 | 11.6 | 86 |

Examples 4–8

The compounds of this invention were synthesized from the title compound of Preparation 6 following the procedure of example 1 and using the corresponding reactant respectively. The ESI/MS data, HPLC retention times and yields are summarised in Table 4.

TABLE 4

| Example | Molecular Formula | ESI/MS m/e [M + H]$^+$ | Retention Time (min.) | Yield % |
|---|---|---|---|---|
| 4 | $C_{25}H_{33}N_7O_4S$ | 528 | 12.1 | 78 |
| 5 | $C_{25}H_{33}N_7O_4S$ | 528 | 12.0 | 80 |
| 6 | $C_{25}H_{33}N_7O_5S$ | 544 | 11.8 | 75 |
| 7 | $C_{25}H_{33}N_7O_5S$ | 544 | 12.1 | 77 |
| 8 | $C_{24}H_{31}N_7O_4S$ | 514 | 12.0 | 72 |

Examples 9–24

The compounds of this invention were synthesized from the title compound of Preparation 3 following the procedure of example 1 and using the corresponding reactant respectively. The ESI/MS data, HPLC retention times and yields are summarised in Table 5.

TABLE 5

| Example | Molecular Formula | ESI/MS m/e [M + H]$^+$ | Retention Time (min.) | Yield % |
|---|---|---|---|---|
| 9 | $C_{22}H_{26}ClN_7O_4S$ | 520 | 12.0 | 75 |
| 10 | $C_{24}H_{30}ClN_7O_4S$ | 548 | 12.0 | 78 |

TABLE 5-continued

| Example | Molecular Formula | ESI/MS m/e [M + H]+ | Retention Time (min.) | Yield % |
|---|---|---|---|---|
| 11 | $C_{24}H_{30}ClN_7O_4S$ | 548 | 11.8 | 80 |
| 12 | $C_{24}H_{30}ClN_7O_5S$ | 564 | 11.7 | 78 |
| 13 | $C_{24}H_{30}ClN_7O_5S$ | 564 | 12.0 | 77 |
| 14 | $C_{25}H_{32}ClN_7O_5S$ | 578 | 12.0 | 81 |
| 15 | $C_{23}H_{28}ClN_7O_4S$ | 534 | 12.0 | 77 |
| 16 | $C_{24}H_{30}ClN_7O_4S$ | 548 | 12.3 | 67 |
| 17 | $C_{21}H_{21}ClN_6O_4S$ | 488 | 16.3 | 32 |
| 18 | $C_{25}H_{30}ClN_7O_4S$ | 560 | 13.2 | 72 |
| 19 | $C_{25}H_{32}ClN_7O_4S$ | 562 | 12.5 | 80 |
| 20 | $C_{25}H_{32}ClN_7O_5S$ | 578 | 12.8 | 85 |
| 21 | $C_{25}H_{32}ClN_7O_4S$ | 562 | 12.7 | 68 |
| 22 | $C_{23}H_{28}ClN_7O_4S$ | 534 | 12.4 | 65 |
| 23 | $C_{25}H_{32}ClN_7O_5S$ | 578 | 12.0 | 75 |
| 24 | $C_{26}H_{34}ClN_7O_5S$ | 592 | 13.2 | 76 |

Examples 25–51

The compounds of this invention were synthesized from the title compound of Preparation 7 following the procedure of example 1 and using the corresponding reactant respectively. The ESI/MS data, HPLC retention times and yields are summarised in Table 6.

TABLE 6

| Example | Molecular Formula | ESI/MS m/e [M + H]+ | Retention Time (min.) | Yield % |
|---|---|---|---|---|
| 25 | $C_{23}H_{28}ClN_7O_4S$ | 534 | 12.6 | 70 |
| 26 | $C_{23}H_{27}ClN_6O_5S$ | 535 | 17.7 | 65 |
| 27 | $C_{25}H_{32}ClN_7O_4S$ | 562 | 12.7 | 68 |
| 28 | $C_{23}H_{30}ClN_7O_4S$ | 536 | 12.2 | 62 |
| 29 | $C_{25}H_{32}ClN_7O_4S$ | 562 | 12.5 | 75 |
| 30 | $C_{25}H_{32}ClN_7O_5S$ | 578 | 12.4 | 69 |
| 31 | $C_{25}H_{32}ClN_7O_5S$ | 578 | 12.7 | 62 |
| 32 | $C_{26}H_{34}ClN_7O_4S$ | 576 | 12.6 | 81 |
| 33 | $C_{26}H_{34}ClN_7O_5S$ | 592 | 12.3 | 65 |
| 34 | $C_{26}H_{34}ClN_7O_5S$ | 592 | 12.7 | 78 |
| 35 | $C_{26}H_{28}ClN_7O_4S$ | 570 | 15.5 | 75 |
| 36 | $C_{24}H_{31}ClN_8O_4S$ | 563 | 12.3 | 66 |
| 37 | $C_{24}H_{28}ClN_7O_5S$ | 562 | 16.6 | 70 |
| 38 | $C_{26}H_{34}ClN_7O_5S$ | 592 | 13.2 | 70 |
| 39 | $C_{24}H_{30}ClN_7O_4S$ | 548 | 12.7 | 74 |
| 40 | $C_{26}H_{34}ClN_7O_4S$ | 576 | 13.3 | 57 |
| 41 | $C_{28}H_{38}ClN_7O_4S$ | 604 | 12.9 | 62 |
| 42 | $C_{22}H_{23}ClN_6O_4S$ | 502 | 17.2 | 15 |
| 43 | $C_{26}H_{34}ClN_7O_4S$ | 576 | 12.8 | 52 |
| 44 | $C_{27}H_{36}ClN_7O_5S$ | 606 | 13.8 | 70 |
| 45 | $C_{26}H_{32}ClN_7O_5S$ | 574 | 13.8 | 68 |
| 46 | $C_{26}H_{34}ClN_7O_4S$ | 576 | 13.1 | 69 |
| 47 | $C_{24}H_{30}ClN_7O_4S$ | 548 | 13.2 | 45 |
| 48 | $C_{26}H_{33}ClN_6O_5S$ | 577 | 19.3 | 53 |
| 49 | $C_{21}H_{25}ClN_6O_4S$ | 492 | 18.0 | 59 |
| 50 | $C_{21}H_{25}ClN_6O_5S$ | 508 | 16.0 | 44 |
| 51 | $C_{24}H_{32}ClN_7O_4S$ | 550 | 12.7 | 78 |

Examples 52–56

The compounds of this invention were synthesized from the title compound of Preparation 4 following the procedure of example 1 and using the corresponding reactant respectively. The ESI/MS data, HPLC retention times and yields are summarised in Table 7.

TABLE 7

| Example | Molecular Formula | ESI/MS m/e [M + H]+ | Retention Time (min.) | Yield % |
|---|---|---|---|---|
| 52 | $C_{22}H_{26}BrN_7O_4S$ | 565 | 12.4 | 63 |
| 53 | $C_{24}H_{30}BrN_7O_4S$ | 593 | 12.4 | 75 |
| 54 | $C_{24}H_{30}BrN_7O_5S$ | 609 | 12.1 | 82 |
| 55 | $C_{24}H_{30}BrN_7O_5S$ | 609 | 12.4 | 79 |
| 56 | $C_{23}H_{28}BrN_7O_4S$ | 579 | 12.4 | 80 |

Examples 54–72

The compounds of this invention were synthesized from the title compound of Preparation 8 following the procedure of example 1 and using the corresponding reactant respectively. The ESI/MS data, HPLC retention times and yields are summarised in Table 8.

TABLE 8

| Example | Molecular Formula | ESI/MS m/e [M + H]+ | Retention Time (min.) | Yield % |
|---|---|---|---|---|
| 57 | $C_{25}H_{32}BrN_7O_4S$ | 606 | 12.8 | 66 |
| 58 | $C_{24}H_{30}BrN_7O_4S$ | 592 | 12.7 | 75 |
| 59 | $C_{22}H_{23}BrN_6O_4S$ | 547 | 17.1 | 70 |
| 60 | $C_{21}H_{25}BrN_6O_4S$ | 537 | 17.8 | 66 |
| 61 | $C_{23}H_{27}BrN_6O_5S$ | 579 | 17.7 | 60 |
| 62 | $C_{25}H_{32}BrN_7O_4S$ | 606 | 13.0 | 52 |
| 63 | $C_{25}H_{32}BrN_7O_5S$ | 622 | 12.9 | 78 |
| 64 | $C_{26}H_{34}BrN_7O_5S$ | 636 | 13.7 | 80 |
| 65 | $C_{28}H_{38}BrN_7O_4S$ | 648 | 13.1 | 85 |
| 66 | $C_{26}H_{34}BrN_7O_4S$ | 620 | 16.7 | 78 |
| 67 | $C_{26}H_{32}BrN_7O_4S$ | 618 | 14.1 | 56 |
| 68 | $C_{26}H_{34}BrN_7O_4S$ | 620 | 13.3 | 82 |
| 69 | $C_{24}H_{30}BrN_7O_4S$ | 592 | 13.4 | 42 |
| 70 | $C_{25}H_{32}BrN_7O_4S$ | 606 | 13.0 | 45 |
| 71 | $C_{26}H_{34}BrN_7O_5S$ | 636 | 13.0 | 80 |
| 72 | $C_{25}H_{32}BrN_7O_4S$ | 606 | 13.3 | 48 |

Example 73

7-Bromo-8-{5-[4-(2-hydroxyethyl)piperazine-1-sulfonyl]-2-propoxyphenyl}-6-propyl-6,9-dihydro-5H-pyrrolo[2,3-e][1,2,4]triazolo[4,3-c]pyrimidine-5-one To a mixture of the title compound of Preparation 8 (0.6 g, 1.14 mmol) and triethylamine (0.175 mL, 1.25 mmol) in dichloromethane (30 mL) was added dropwise 1-(2-hydroxy ethyl)piperazine (0.163 g, 1.25 mmol) and the resulting mixture was stirred at room temperature overnight. The reaction mixture was diluted with dichloromethane, washed with aqueous solution of sodium bicarbonate in water, dried (MgSO₄) and evaporated under reduced pressure. The resulting crude residue was triturated with hot methanol and the precipitate collected by filtration and dried under vacuum to yield the title compound (270 mg, 38%).

m.p.: 2671C d(DMSO-d6): 0.98 (m, 6H), 1.74 (m, 4H), 2.38 (t, 2H), 2.50 (m, 4H), 2.92 (m, 4H), 3.44 (q, 2H), 4.09 (t, 2H), 4.36 (m, 3H), 7.41 (d, 1H), 7.65 (d, 1H), 7.81 (dd, 1H), 9.21 (s, 1H), 13.32 (bs, 1H).

Example 74

7-Bromo-8-[5-(piperazine-1-sulfonyl)-2-propoxyphenyl]-6-propyl-6,9-dihydro-5H-pyrrolo[2,3-e][1,2,4]triazolo[4,3-c]pyrimidine-5-one Obtained as a white solid (15%) from the title compound of Preparation 8 and piperazine following the procedure of example 73.

m.p.: 2451C d(DMSO-d6): 0.95 (m, 6H), 1.75 (m, 4H), 2.75 (m, 4H), 2.84 (m, 4H), 4.10 (t, 2H), 4.35 (t, 2H), 7.41 (d, 1H), 7.65 (d, 1H), 7.79 (dd, 1H), 9.21 (s, 1H), 13.2 (bs, 1H).

Examples 75–79

The compounds of this invention were synthesized from the title compound of Preparation 3 following the procedure of example 1 and using the corresponding reactant respectively. The ESI/MS data, HPLC retention times and yields are summarised in Table 9.

TABLE 9

| Example | Molecular Formula | ESI/MS m/e [M + H]+ | Retention Time (min.) | Yield % |
|---|---|---|---|---|
| 75 | $C_{25}H_{30}ClN_7O_4S$ | 560 | 8.2 | 65 |
| 76 | $C_{25}H_{30}ClN_7O_4S$ | 560 | 8.3 | 72 |
| 77 | $C_{26}H_{32}ClN_7O_4S$ | 574 | 8.1 | 75 |
| 78 | $C_{25}H_{30}ClN_7O_5S$ | 576 | 8.2 | 42 |
| 79 | $C_{24}H_{28}ClN_7O_4S$ | 546 | 7.9 | 60 |

Examples 80–83

The compounds of this invention were synthesized from the title compound of Preparation 8 following the procedure of example 1 and using the corresponding reactant respectively. The ESI/MS data, HPLC retention times and yields are summarised in Table 10.

TABLE 10

| Example | Molecular Formula | ESI/MS m/e [M + H]+ | Retention Time (min.) | Yield % |
|---|---|---|---|---|
| 80 | $C_{26}H_{32}BrN_7O_4S$ | 619 | 8.8 | 82 |
| 81 | $C_{27}H_{34}BrN_7O_4S$ | 633 | 8.7 | 78 |
| 82 | $C_{26}H_{32}BrN_7O_5S$ | 635 | 8.9 | 51 |
| 83 | $C_{25}H_{30}BrN_7O_4S$ | 605 | 8.5 | 88 |

Examples 84–88

The compounds of this invention were synthesized from the title compound of Preparation 9 following the procedure of example 1 and using the corresponding reactant respectively. The ESI/MS data, HPLC retention times and yields are summarised in Table 11.

TABLE 11

| Example | Molecular Formula | ESI/MS m/e [M + H]+ | Retention Time (min.) | Yield % |
|---|---|---|---|---|
| 84 | $C_{26}H_{32}IN_7O_4S$ | 666 | 8.5 | 77 |
| 85 | $C_{26}H_{32}IN_7O_4S$ | 666 | 8.5 | 85 |
| 86 | $C_{27}H_{34}IN_7O_4S$ | 680 | 8.5 | 62 |
| 87 | $C_{26}H_{32}IN_7O_5S$ | 682 | 8.8 | 35 |
| 88 | $C_{25}H_{30}IN_7O_4S$ | 652 | 8.4 | 75 |

The following examples illustrate pharmaceutical compositions according to the present invention and procedures for their preparation.

Composition Example 1

50,000 capsules each containing 100 mg of active ingredient were prepared according to the following formulation:

| | |
|---|---|
| Active ingredient | 5 Kg |
| Lactose monohydrate | 10 Kg |
| Colloidal silicone dioxide | 0.1 Kg |
| Corn starch | 1 Kg |
| Magnesium stearate | 0.2 Kg |

Procedure

The above ingredients were sieved through a 60 mesh sieve, and were loaded into a suitable mixer and filled into 50,000 gelatine capsules.

Composition Example 2

50,000 Tablets each containing 50 mg of active ingredient were prepared from the following formulation:

| | |
|---|---|
| Active ingredient | 2.5 Kg |
| Microcrystalline cellulose | 1.95 Kg |
| Spray dried lactose | 9.95 Kg |
| Carboxymethyl starch | 0.4 Kg |
| Sodium stearyl fumarate | 0.1 Kg |
| Colloidal silicon dioxide | 0.1 Kg |

Procedure

All the powders were passed through a screen with an aperture of 0.6 mm, then mixed in a suitable mixer for 20 minutes and compressed into 300 mg tablets using 9 mm disc and flat bevelled punches. The disintegration time of the tablets was about 3 minutes.

What is claimed is:

1. A compound of formula (I):

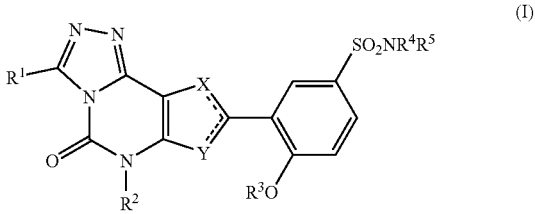

wherein: —X—C—Y— represents

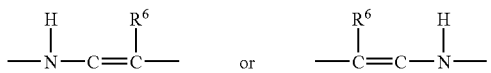

R$^1$, R$^2$ and R$^3$ each independently represent: hydrogen; an alkyl group which is unsubstituted or substituted by hydroxy, alkoxy, alkylthio, amino, mono- or di-alkylamino, hydroxycarbonyl, alkoxycarbonyl, acylamino, carbamoyl or alkylcarbamoyl groups; or a group of formula

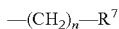

wherein n is an integer from 0 to 4 and R$^7$ represents: a cycloalkyl group which may be unsubstituted or substituted by one or more halogen atoms or alkyl, hydroxy, alkylenedioxy, alkoxy, amino, mono- or di-alkylamino, alkylamido, nitro, cyano or trifluoromethyl groups; a phenyl group which may be unsubstituted or substituted by one or more halogen atoms or alkyl, hydroxy, alkylenedioxy, alkoxy, amino, mono- or di-alkylamino, nitro, cyano or -trifluoromethyl groups; or a 3 to 7-membered ring comprising from 1 to 4 heteroatoms selected from nitrogen, oxygen and sulphur, which ring may be unsubstituted or substituted by one or more halogen atoms or hydroxy, alkoxy, phenyl, alkoxycarbonyl, amino, mono-alkylamino, di-alkylamino or hydroxycarbonyl groups or one or more alkyl groups which may be unsubstituted or substituted by one or more halogen atoms or hydroxy, alkoxy, hydroxyalkoxy, phenyl, alkoxycarbonyl, amino, mono- or di-alkylamino or hydroxycarbonyl groups, either R$^4$ and R$^5$ together with the nitrogen atom to which they are attached form a 3 to 7-membered ring comprising a total of from 1 to 4 heteroatoms selected from nitrogen, oxygen and sulphur, which ring may be unsubstituted or substituted by one or more halogen atoms or hydroxy, oxoalkyl, carbamoyl, hydroxycarbonyl, alkoxycarbonyl, trifluoroacetyl, amino, mono- or di-alkylamino groups and/or an alkylene group and/or one or more alkyl groups, wherein said alkylene group and said alkyl groups may in turn be unsubstituted or substituted by one or more hydroxy, alkoxy, hydroxyalkoxy, amino or mono- or di-alkylamino groups, or R$^4$ and R$^5$ independently represent hydrogen, an amidino group or an alkyl, alkenyl or alkynyl group which may be unsubstituted or substituted by one or more halogen atoms or hydroxy, alkoxy, alkylthio, amino, mono- or di-alkylamino groups, or R$^4$ represents hydrogen or an alkyl group and R$^5$ represents a group of formula —(CH$_2$)$_n$—R$^7$ wherein n and R$^7$ are defined above, and R$^6$ represents a hydrogen or halogen atom, or a nitro or alkoxycarbonyl group, or an alkyl group which is unsubstituted or substituted by one or more hydroxy, alkoxy, alkylthio, amino, mono- or di-alkylamino, hydroxycarbonyl, alkoxycarbonyl, acylamino, carbamoyl or alkylcarbamoyl groups, or a pharmaceutically acceptable salt thereof.

2. A compound according to claim 1 wherein R$^1$ represents: hydrogen; a C$_1$–C$_4$ alkyl group; or a group of formula

3. A compound according to claim 1 wherein R$^2$ represents: a C$_1$–C$_5$ alkyl group; a substituted C$_1$–C$_5$ alkyl group; a C$_{3-10}$ cycloalkyl group; or a group of formula

wherein n is 0, 1 or 2 and R$^7$ represents an unsubstituted or substituted phenyl or pyridyl group.

4. A compound according to claim 1 wherein R$^3$ represents: a C$_1$–C$_4$ alkyl group; a C$_{3-10}$ cycloalkyl group; or a group of formula

wherein n is 0, 1 or 2 and R$^7$ represents an unsubstituted or substituted phenyl or pyridyl group.

5. A compound according to claim 1 wherein R$^4$ and R$^5$ together with the nitrogen atom to which they are attached form a piperidyl, pyrrolidyl, azetidinyl, aziridyl, piperazinyl, [1,4]diazepan-1-yl, morpholinyl, thiomorpholinyl, pyrrolyl, pyrazolyl, imidazolyl, imidazolidinyl, pyrazolinyl or group, which is unsubstituted or substituted by an alkylene group and/or from 1 to 3 groups independently selected from C$_1$–C$_4$ alkyl, C$_2$–C$_4$ alkenyl, carbamoyl, amino, di-C$_1$–C$_4$-alkylamino, (2-hydroxyethyl)methylamino, hydroxyl, 2,2,2-trifluoroethanoyl, 2,2,2-trifluoroethyl, carbaldehyde groups and hydroxyalkyl groups, alkoxycarbonyl groups, alkoxyalkyl groups and hydroxyalkoxyalkyl groups wherein the alkyl moieties contain from 1 to 4 carbon atoms, and wherein said alkylene group may in turn be unsubstituted or substituted by one or more hydroxy, alkoxy, hydroxyalkoxy, amino or mono- or di-alkylamino groups.

6. A compound according to claim 1 wherein R$^4$ and R$^5$ independently represent hydrogen or a propynyl group, an amidino group or a C$_1$–C$_4$ alkyl group which is unsubstituted or substituted by a hydroxy, methyl or dimethylamino group.

7. A compound according to claim 1 wherein wherein R$^5$ is a group of formula

wherein n is 0, 1, 2 or 3 and R$^8$ is a pyridyl, piperidyl, piperazinyl, morpholinyl, triazolyl, tetrazolyl, pyrrolidinyl, 1-ethylaminocyclohex-1-yl, 1-diethylaminocyclohex-1-yl, 1-ethylaminocyclohept-1-yl, 1-diethylaminocyclohept-1-yl, 3,4-dimethoxyphenyl, 1-methyl-4-phenylpiperidin-4-yl, imidazoyl, 1-methylpiperid-4-yl, tetrahydrofuranyl, 2,2,6,6-tetramethylpiperid-4-yl, 4-hydroxypiperid-4-yl, 1-acetamidocyclohept-1-yl, 1-methyl-3-azetidinyl or 4-methylpiperazin-1-yl group.

8. A compound according claim 1 wherein R$^6$ represents a fluorine, chlorine, bromine or hydrogen atom or a methyl, ethyl, n-propyl, n-butyl, methoxycarbonyl, ethoxycarbonyl, or nitro group.

9. A compound according to claim 1 which is:
7-Chloro-8-[2-ethoxy-5-(4-methyl-[1,4]diazepane-1-sulfonyl)phenyl]-6-propyl-6,9-dihydro-5H-pyrrolo[2,3-e][1,2,4]triazolo[4,3-c]pyrimidine-5-one claim 1 or a pharmaceutically acceptable salt thereof and a pharmaceutically acceptable excipient.

10. A compound of formula (VI):

(VI) [structure]

wherein $R^1$, $R^2$, $R^3$ and $R^6$ are as defined in claim 1.

11. A compound of formula (IX):

(IX) [structure]

wherein $R^2$, $R^3$ and $R^6$ are as defined in claim 1.

12. A compound of formula (XIV):

(XIV) [structure]

wherein $R^2$, $R^3$, $R^4$, $R^1$ and $R^6$ are as defined in claim 1.

13. A pharmaceutical composition comprising as an active ingredient, at least one compound as defined in any one of claims 1 to 10 or a pharmaceutically acceptable salt thereof and a pharmaceutically acceptable excipient.

14. A process for producing a compound of formula (I):

(I) [structure]

wherein: —X—C—Y— represents $$-N-C=C-$$
with H on N and $R^6$ on C $R^1$, $R^2$, $R^3$, $R^4$, $R^1$ and $R^6$ are as defined in claim 1, which process comprises reacting a compound of formula (IV):

(IV) [structure]

wherein $R^1$, $R^2$, $R^3$ and $R^6$ are as defined in claim 1 with an amine of formula (V):

(V) [structure]

wherein $R^4$ and $R^5$ are as defined in claim 1.

15. A process for producing a compound of formula (I):

(I) [structure]

wherein: —X—C—Y— represents $$-C=C-N-$$
with $R^6$ on C and H on N and $R^1$, $R^2$, $R^3$, $R^4$, $R^5$ and $R^6$ are as defined in claim 1, which process comprises reacting a compound of formula (XIII):

(XIII) [structure]

wherein $R^2$, $R^3$, $R^4$, $R^1$ and $R^6$ are as defined in claim 1 with a carboxylic acid of formula (VIII):

$R^1$—COOH  (VIII)

wherein $R^1$ is as defined in claim 1, or a reactive derivative thereof.

* * * * *